(12) United States Patent
Condon et al.

(10) Patent No.: US 10,034,912 B2
(45) Date of Patent: *Jul. 31, 2018

(54) SMAC MIMETIC

(71) Applicant: TetraLogic Birinapant UK Ltd., Birmingham (GB)

(72) Inventors: Stephen M. Condon, Glenmoore, PA (US); Yijun Deng, Dresher, PA (US); Matthew G. Laporte, Honeybrook, PA (US); Susan R. Rippin, Wilmington, DE (US)

(73) Assignee: TetraLogic Birinapant UK Ltd., Birmingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,813

(22) Filed: Nov. 7, 2016

(65) Prior Publication Data

US 2017/0182116 A1  Jun. 29, 2017

Related U.S. Application Data

(60) Continuation of application No. 14/607,752, filed on Jan. 28, 2015, which is a continuation of application No. 14/075,190, filed on Nov. 8, 2013, now Pat. No. 8,986,993, which is a continuation of application No. 13/611,274, filed on Sep. 12, 2012, now Pat. No. 8,603,816, which is a division of application No. 12/819,221, filed on Jun. 20, 2010, now Pat. No. 8,283,372.

(60) Provisional application No. 61/222,668, filed on Jul. 2, 2009.

(51) Int. Cl.
| | | |
|---|---|---|
| *A61K 38/07* | (2006.01) |
| *A61K 45/06* | (2006.01) |
| *A61K 38/05* | (2006.01) |
| *A61K 31/555* | (2006.01) |

(52) U.S. Cl.
CPC ............ *A61K 38/05* (2013.01); *A61K 31/555* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,832,253 A | 8/1974 | DiPalma et al. |
| 3,854,480 A | 12/1974 | Zaffaroni |
| 4,278,793 A | 7/1981 | Durckheimer et al. |
| 4,452,775 A | 6/1984 | Kent |
| 4,496,658 A | 1/1985 | Kondo et al. |
| 4,525,300 A | 6/1985 | Yoshida et al. |
| 4,667,014 A | 5/1987 | Nestor, Jr. et al. |
| 4,748,034 A | 5/1988 | de Rham |

(Continued)

FOREIGN PATENT DOCUMENTS

| | | |
|---|---|---|
| WO | 1999/015657 A2 | 4/1999 |
| WO | 2002/016418 A2 | 2/2002 |

(Continued)

OTHER PUBLICATIONS

Wyllie et al., Cell Death: the significance of apoptosis, 1980, Int. Rev. Cytol. 68:251-306.

Wu et al., Structural basis of IAP recognition by Smac/DIABLO, 2000, Nature 408:1008-1012.

Vucic et al., ML-IAP, a novel inhibitor of apoptosis that is preferentially expressed in human melanomas, 2000, Curr. Biol. 10:1359-1366.

Verhagen et al., Identification of DIABLO, a Mammalian Protein that Promotes Apoptosis by Binding to and Antagonizing IAP Proteins, 2000, Cell 102:43-53.

(Continued)

*Primary Examiner* — Anna Pagonakis
(74) *Attorney, Agent, or Firm* — Banner & Witcoff, Ltd.

(57) ABSTRACT

A SMAC mimetic and pharmaceutical compositions thereof and methods of use.

17 Claims, 2 Drawing Sheets

*Mortality at 3 mg/kg
**Mortality at 10 mg/kg

(56) References Cited

U.S. PATENT DOCUMENTS

| | | | |
|---|---|---|---|
| 4,935,493 | A | 6/1990 | Bachovchin et al. |
| 5,023,077 | A | 6/1991 | Gevas et al. |
| 5,075,109 | A | 12/1991 | Tice et al. |
| 5,239,660 | A | 8/1993 | Ooi |
| 5,358,934 | A | 10/1994 | Borovsky et al. |
| 5,468,494 | A | 11/1995 | Gevas et al. |
| 5,527,775 | A | 6/1996 | Shorr et al. |
| 5,545,719 | A | 8/1996 | Shashoua |
| 5,578,710 | A | 11/1996 | Ambrosius et al. |
| 5,660,811 | A | 8/1997 | Mills |
| 5,688,506 | A | 11/1997 | Grimes et al. |
| 5,766,572 | A | 6/1998 | Hasegawa et al. |
| 5,831,002 | A | 11/1998 | Haupt et al. |
| 6,110,691 | A | 8/2000 | Wang et al. |
| 6,133,437 | A | 10/2000 | Korneluk et al. |
| 6,187,557 | B1 | 2/2001 | Rothe et al. |
| 6,338,835 | B1 | 1/2002 | Shochat et al. |
| 6,608,026 | B1 | 8/2003 | Wang et al. |
| 6,911,426 | B2 | 6/2005 | Reed et al. |
| 6,992,063 | B2 | 1/2006 | Shi |
| 7,217,688 | B2 | 5/2007 | Reed et al. |
| 7,244,851 | B2 | 7/2007 | Cohen et al. |
| 7,309,792 | B2 | 12/2007 | Harran et al. |
| 7,456,209 | B2 | 11/2008 | Condon et al. |
| 7,517,906 | B2 | 4/2009 | Condon et al. |
| 7,579,320 | B2 | 8/2009 | Boudreault et al. |
| 7,589,118 | B2 | 9/2009 | Laurent et al. |
| 7,718,600 | B2 | 5/2010 | McLendon et al. |
| 7,799,782 | B2 | 9/2010 | Munson et al. |
| 7,807,699 | B2 | 10/2010 | Hanson et al. |
| 7,968,590 | B2 | 6/2011 | Condon et al. |
| 7,985,735 | B2 | 7/2011 | Condon et al. |
| 8,022,230 | B2 | 9/2011 | Condon et al. |
| 8,143,426 | B2 | 3/2012 | Condon et al. |
| 8,283,372 | B2 | 10/2012 | Condon et al. |
| 8,399,683 | B2 | 3/2013 | Condon et al. |
| 8,415,486 | B2 | 4/2013 | Condon et al. |
| 8,481,495 | B2 | 7/2013 | Condon et al. |
| 8,497,297 | B2 | 7/2013 | Condon et al. |
| 8,603,816 | B2 | 12/2013 | Condon et al. |
| 8,802,716 | B2 | 8/2014 | Condon et al. |
| 8,822,525 | B2 | 9/2014 | Condon et al. |
| 8,986,993 | B2 | 3/2015 | Condon et al. |
| 9,187,490 | B2 | 11/2015 | Condon et al. |
| 2002/0132786 | A1 | 9/2002 | Alnemri |
| 2002/0160975 | A1 | 10/2002 | Alnemri |
| 2002/0177557 | A1 | 11/2002 | Shi |
| 2004/0054148 | A1 | 3/2004 | Alnemri et al. |
| 2005/0197403 | A1 | 9/2005 | Harran et al. |
| 2005/0234042 | A1 | 10/2005 | Palermo et al. |
| 2005/0261203 | A1 | 11/2005 | Cohen et al. |
| 2006/0014700 | A1 | 1/2006 | Cohen et al. |
| 2006/0025347 | A1 | 2/2006 | Condon et al. |
| 2006/0052311 | A1 | 3/2006 | Sharma et al. |
| 2006/0128632 | A1 | 6/2006 | Sharma et al. |
| 2006/0167066 | A1 | 7/2006 | Cohen et al. |
| 2006/0194741 | A1 | 8/2006 | Condon et al. |
| 2006/0258581 | A1 | 11/2006 | Reed et al. |
| 2006/0264379 | A1 | 11/2006 | Jarvis et al. |
| 2007/0003535 | A1 | 1/2007 | Reed et al. |
| 2007/0042428 | A1 | 2/2007 | Springs et al. |
| 2007/0093428 | A1 | 4/2007 | Laurent |
| 2007/0093429 | A1 | 4/2007 | Laurent et al. |
| 2007/0203749 | A1 | 8/2007 | Chunduru et al. |
| 2008/0020986 | A1 | 1/2008 | Condon et al. |
| 2008/0089896 | A1 | 4/2008 | Wang et al. |
| 2008/0119532 | A1 | 5/2008 | Harran et al. |
| 2008/0269140 | A1 | 10/2008 | Wang et al. |
| 2009/0005411 | A1 | 1/2009 | Jensen et al. |
| 2009/0048183 | A1 | 2/2009 | Condon et al. |
| 2009/0104151 | A1 | 4/2009 | Hanson et al. |
| 2009/0123480 | A1 | 5/2009 | Wang et al. |
| 2009/0142334 | A1 | 6/2009 | Korneluk et al. |
| 2009/0192140 | A1 | 7/2009 | Laurent et al. |
| 2009/0221630 | A1 | 9/2009 | Koehler et al. |
| 2010/0075911 | A1 | 3/2010 | Condon et al. |
| 2010/0130539 | A1 | 5/2010 | Koehler |
| 2011/0003877 | A1 | 1/2011 | Condon et al. |
| 2011/0008802 | A1 | 1/2011 | Alavi et al. |
| 2011/0288116 | A1 | 11/2011 | Condon et al. |
| 2011/0294827 | A1 | 12/2011 | Condon et al. |
| 2011/0301151 | A1 | 12/2011 | Condon et al. |
| 2011/0305777 | A1 | 12/2011 | Condon et al. |
| 2012/0015352 | A1 | 1/2012 | Leverkus et al. |
| 2012/0094917 | A1 | 4/2012 | Condon et al. |
| 2012/0135990 | A1 | 5/2012 | Condon et al. |
| 2013/0012564 | A1 | 1/2013 | Condon et al. |
| 2013/0196927 | A1 | 8/2013 | Benetatos et al. |
| 2013/0289075 | A1 | 10/2013 | Condon et al. |
| 2014/0073579 | A1 | 3/2014 | Condon et al. |
| 2014/0243276 | A1 | 8/2014 | Weng et al. |
| 2014/0303090 | A1 | 10/2014 | Condon et al. |
| 2014/0329823 | A1 | 11/2014 | Condon et al. |
| 2015/0158908 | A1 | 6/2015 | Condon et al. |
| 2015/0190470 | A1 | 7/2015 | Begley et al. |
| 2015/0307448 | A1 | 10/2015 | Condon et al. |

FOREIGN PATENT DOCUMENTS

| | | |
|---|---|---|
| WO | 2002/026775 A2 | 4/2002 |
| WO | 2002/030959 A2 | 4/2002 |
| WO | 2002/096930 A2 | 12/2002 |
| WO | 2003/018014 A2 | 3/2003 |
| WO | 2004/005248 A1 | 1/2004 |
| WO | 2004/007529 A2 | 1/2004 |
| WO | 2004/072105 A2 | 8/2004 |
| WO | 2005/069888 A2 | 8/2005 |
| WO | 2005/069894 A2 | 8/2005 |
| WO | 2005/074989 A2 | 8/2005 |
| WO | 2005/084317 A2 | 9/2005 |
| WO | 2005/094818 A1 | 10/2005 |
| WO | 2005/097791 A1 | 10/2005 |
| WO | 2006/010118 A2 | 1/2006 |
| WO | 2006/014361 A1 | 2/2006 |
| WO | 2006/017295 A2 | 2/2006 |
| WO | 2006/020060 A2 | 2/2006 |
| WO | 2006/069063 A1 | 6/2006 |
| WO | 2006/091972 A2 | 8/2006 |
| WO | 2006/122408 A1 | 11/2006 |
| WO | 2006/128455 A2 | 12/2006 |
| WO | 2006/133147 A2 | 12/2006 |
| WO | 2007/021825 A2 | 2/2007 |
| WO | 2007/048224 A1 | 5/2007 |
| WO | 2007/101347 A1 | 9/2007 |
| WO | 2007/106192 A2 | 9/2007 |
| WO | 2007/130626 A2 | 11/2007 |
| WO | 2007/131365 A1 | 11/2007 |
| WO | 2007/136921 A2 | 11/2007 |
| WO | 2008/014238 A2 | 1/2008 |
| WO | 2008/014240 A2 | 1/2008 |
| WO | 2008014229 A2 | 1/2008 |
| WO | 2008014236 A1 | 1/2008 |
| WO | 2008/016893 A1 | 2/2008 |
| WO | 2008/057172 A2 | 5/2008 |
| WO | 2008/134679 A1 | 11/2008 |
| WO | 2010/033531 A1 | 3/2010 |
| WO | 2014121178 A1 | 8/2014 |

OTHER PUBLICATIONS

Vucic et al., Inhibition of Reaper-induced apoptosis by interaction with inhibitor of apoptosis proteins (IAPS), 1997, Proc. Natl. Acad. Sci. USA 94:10183-10188.

Verdecia et al. Structure of the human anti-apoptotic protein surviving reveals a dimeric arrangement, 2000, Nat. Struc. Biol. 7(7):602-608.

Wang et al., The *Drosphila* Caspase Inhibitor DIAP1 is Essential for Cell Survival and Is Negatively Regulated by HID, 1999, Cell 98:453-463.

Vucic et al., Engineering ML-IAP to produce an extraordinarily potent caspase 9 inhibitor: implications for Smac? dependent antiapoptotic activity of ML-IAP, 2005, Biochem. J. 385(1):11-20.

(56) References Cited

OTHER PUBLICATIONS

Zuckerman et al., Efficient Method for the Preparation of Peptoids [Oligo(N-substituted glycines)] by Submonomer Solid-Phase Synthesis, 1992, J. Am. Chem. Soc. 114:10646-10647.
Kasof et al., Livin, a Novel Inhibitor of Apoptosis Protein Family Member, 2001, J. Biol. Chem. 276(5):3238-3246.
Hansen et al., Re-examination and further development of a precise and rapid dye method for measuring cell growth/cell kill, 1989, J. Immunol. Methods, 119:203-210.
Bockbrader et al., "A small molecule Smac-mimic compound induces apoptosis and sensitizes TRAIL-and etoposide-induced apoptosis in breast cancer cells," Oncogene, 2005, vol. 24, No. 49, pp. 7381-7388.
Fotin-Mleczek et al., "Cationic cell-penetrating peptides interfere with TNF signalling by induction of TNF receptor internalization," Journal of Cell Science, 2005, vol. 118, No. 15, pp. 3339-3351.
Extended European Search Report dated Apr. 5, 2013 in European App. No. 10794587.
Li et al., A small molecule Smac potentiates TRAIL-andTNF?-medicated cell death, Science, vol. 305, 2004, pp. 1471-1474.
Nikolovsak-Coleska et al., Development and optimization of a binding assay for the XIAP BIR3 domain using fluorescence polarization, 2004, Anal. Biochem. 332:261-273.
Wyllie, Glucocorticoid-induced thymocyte apoptosis is associated with endogenous endonuclease activation, 1981, Nature 284:555-556.
Hunter, A.M. et al., "The inhibitors of apoptosis (IAPs) as cancer targets," Apoptosis 12:1542-1568 (2007).
Dean et al., "Novel therapeutic targets in lunch cancer: Inhibitor apoptosis proteins from laboratory to clinic," Cancer Treat. Rev. 33:203-212 (2007).
Sykes et al., "Treatment of severe autoimmune disease by stem-cell transplantation," Nature 435:620-627 (2005).
Tarner et al., "Treatment of autoimmune diases by adoptive cellular gene therapy," Ann. N.Y. Acad. Sci. 998:512-519 (2003).
Traub al., "Psoriasis-pathophysiology, conventional, and alternative approaches to treatment," Alt. Med. Rev. 112:319-330 (2007).
George, "Management of patients with refractory immune thrombocytopenic purpura," J. Throm. Haemost. 4:1664-1672 (2006).
Boxrud et al., Streptokinase Binds to Human Plasmin with High Affinity, Perturbs the Plasmin Active Site, and Induces Expression of a Substrate Recognition Exosite for Plasminogen, 2000, J. Biol. Chem. 275(19)14579-14589.
McLendon et al., CAS: 152:568466, 2010.
International Search Report and Written Opinion in International Applicationno. PCT/US10/399976, 9 pages, dated Aug. 31, 2010.
Ashhab et al., Two splicing variants of a new inhibitor of apoptosis gene with different biological properties and tissue distribution pattern, 2001, FEBS Lett. 495:56-60.
Wu et al., Structural Analysis of a Functional DIAP1 Fragment Bound to Grim and Hid Peptides, 2001, Mol. Cell 8:95-104.
Li et al., A small molecule Smac mimic potentiates TRAIL- and TNF.alpha.-medicated cell death, Science, vol. 305 (2004), pp. 1471-1474.
Kushner, D. J. et al., "Pharmacological uses and perspectives of heavy water and deuterated compounds," Canadian Journal of Physiology and Pharmacology, Canada, Feb. 1, 1999, V. 77 N. 2, p. 79-88.
(JP) Office Action issued in Application No. 2012-518560, Mar. 31, 2013.
Schlenk, Richard F. et al., "Mutations and Treatment Outcome in Cytogenetically Normal Acute Myeloid Leukemia," N. Engl. J. Med. 358;18, May 1, 2008.
"TetraLogic Pharmaceuticals Announces Data on Lead Clinical Programs," TetraLogic press release, retrieved from https://beta.finance.yahoo.com/news/tetralogic-pharmaceuticals-announces-data-lead-211127969.html, Jan. 6, 2016.
The chemical abstract service entry for registry No. 1260251-31-7, Jan. 24, 2011.
Moore, Mitchell M., "Abstract B163: Pharmacokinetic analysis and preclinical evaluation of the SMAC mimetic TL32711 in an orthotopic human breast tumor xenograft model," Mol. Cancer Ther., doi:10.1158/1535-7163.TARG-09-B163, Dec. 2009.
Le Tourneau, Christophe et al., "Dose Escalation Methods in Phase I Cancer Clinical Trials," J. Natl. Cancer Inst., vol. 101, Issue 10, p. 708-720, May 20, 2009.
Carter, Bing Z. et al., "Small-molecule XIAP inhibitors derepress downstream effector caspases and induce apoptosis of acute myeloid leukemia cells," Blood, doi: 10.1182/blood-2004-08-3168, Feb. 1, 2005.
Clinical Trial "Dose Escalation Safety Study of TL32711 in Adults with Refractory Solid Tumors or Lymphoma," Study started Nov. 2009 and completed Mar. 2013, retrieved from https://www.clinicaltrials.gov/ct2/show/NCT00993239?term=NCT00993239&rank=1.
Ambrosini et al., Induction of Apoptosis and Inhibition of Cell Proliferation by survivin Gene Targeting, 1998, J. Biol. Chem. 273(18):11177-11182.
Brunger, X-PLOR, A System for Crystallography and NMR, Yale University Press, New Haven, CT, 1991.
Craig et al., Modern Pharmacology with Clinical Applications, 6th Ed., Lippincott Williams & Wilkins, Philadelphia, pp. 639-656, 2004.
Chawla-Sarkar, Preferential Induction of Apoptosis by Interferon (IFN)-? Compared with IFN-?2: Correlation with TRAIL/Apo2L Induction in Melanoma Cell Lines, 2001, Clin. Can. Res. 7:1821-1831.
Chai et al., Structural and biochemical basis of apoptotic activation by Smac/DIABLO, 2000, Nature 406:855-862.
Chan et al., Fmoc Solid Phase Peptide Synthesis: A Practical Approach, 2000, Oxford University Press (TOC).
Chen et al., Grim, a novel cell death gene in *Drospohila*, 1996, Genes & Devel. 10:1773-1782.
Chantalat et al., Crystal Structure of Human Survivin Reveals a Bow Tie-Shaped Dimer with Two Unusual ?—Helical Extensions, 2000, Mol. Cell. 6:183-189.
Deveraux et al., IAP family proteins-suppressors of apoptosis, 1999, Genes & Devel. 13:239-252.
Du et al., Smac, a mitochondrial Protein that Promotes Cytochrome c-Dependent Caspase Activation by Eliminating IAP Inhibitiion, 2000, Cell 102:33-42.
Deveraux et al., Cleavage of human inhibitor of apoptosis protein XIAP results in fragments with distinct specificities for caspases, 1999, EMBO J. 18(19):5242-5251.
Fulda et al., Smac agonists sensitize for Apo2L /TRAIL-or anticancer drug-induced apoptosis and induce regression of malignant glioma in vivo, 2002, Nat. Med. 8(8):808-815.
Freidinger et al., Synthesis of 9pflourenylmethyloxycarbobyl-protected N-alkyl amino acids by reduction of oxazolidinones, 1983, J. Org. Chem. 48:77-81.
Hruby et al., Synthesis of oligopeptide and peptidomimetic libraries, 1997, Cuff. Op. in Chem. Biol. 1:114-119.
Hruby et al., Conformational and Topographical Considerations in Designing Agonist Peptidomimetics from Peptide Leads, 2000, Curr. Med. Chem. 7(9):945-970.
Hay, Understanding IAP function and regulation: a view from *Drosophila*, 2000, Cell Death and Diff. 7:1045-1056.
Hiratsuka, ATP-induced Opposite Changes in the Local Environments around Cys697(SH2) and Cys707(SH1) of the Myosin Motor Domain Revealed by the Prodan Fluorescence, 1999, J. Biol. Chem. 274(41):29156-29163.
Goyal et al., Induction of apoptosis by *Drosophila* reaper, hid and grim through inhibition of IAP function, 2000, EMBO J. 19(4):589-597.
Hengartner, Programmed cell death in invertebrates, 1996, Curr. Opin. Genet. Dev. 6:34-38.
Horvitz, Genetic Control of Programmed Cell Death in the Nematode Caenorhabditis elegans, 1999, Can. Res. 59:1701s-1706s.
Hirel et al., Extent of N-terminal methionine excision from *Escherichia coli* proteins is governed by the side-chain length of the penultimate amino acid, 1989, Proc. Natl. Acad. Sci. USA 86:8247-8251.

(56) References Cited

OTHER PUBLICATIONS

Kohli et al., SMAC/Diablo-dependent apoptosis induced by nonsteroidal antiinflammatory drugs (NSAIDs) in colon cancer cells, 2004, PNAS 101(48):16897-16902.
Jacobson et al., Programmed Cell Death in Animal Development, 1997, Cell 88:347-354.
Jones et al., Improved methods for building protein models in electron density maps and the location of errors in these models, 1991, Acta Crystallogr. A47:110-119.
Kraulis, Molscript: a program to produce both detailed and schematic plots of protein structures, 1991, J. Appl. Crystallogr. 24:946-950.
Macor et al., The Synthesis of a Conformationally Restricted Analog of the Anti-Migraine Drug Sumatriptan, 1992, Tetrahedron Lett. 33(52):8011-8014.
Lange's Handbook of Chemistry, Dean ed., Table 7-2, 1985.
Lisi et al., Diverse Domains of THREAD/DIAP1 are Required to Inhibit Apoptosis Induced by REAPER and HID in *Drosophila*, 1999, Genetics Soc. Am. 154:669-678.
Liu, Structural basis for binding of Smac/DIABLO to the XIAP BIR3 domain, Dec. 2000, Nature, pp. 1004-1008.
McCarthy et al., Apoptosis induced by *Drosophila* reaper and grim in a human system, 1999, J. Biol. Chem. 273 (37):24009-24015.
Morgan et al., Approaches to the Discovery of Non-Peptide Ligands for Peptide Receptors and Peptidases, 1989, Ann. Rep. Med. Chem. 243-252.
Miller, An exegesis of IAPs: salvation and surprises from BIR motifs, 1999, Cell Biol. 9:323-328.
Owenius et al., Properties of Spin and Fluorescent Labels at a Receptor-Ligand Interface, 1999, Biophys. J. 77:2237-2250.
Navaza, AmoRe: an Automated Package for Molecular Replacement, 1994, Acta Cryst. A50:157-163.
Nicholls et al., Protein folding and association: insights from the interfacial and thermodynamic properties of hydrocarbons, 1991, Proteins: Struct. Funct. & Genet. 11:281-296.
Oost et al., Discovery of Potent Antagonists of the Antiapoptotic Protein XIAP for the Treatment of Cancer, 2004.
Park et al., Non-peptide small molecule inhibitors of XIAP, 2004, Bioorganic & Med. Chem. Lett. 15:771-775.
Ripka et al., Peptidomimetic design, 1998, Curr. Op. Chem. Biol. 2:441-452.
Hoffman, "Organic Chemistry: An Intermediate Text," Second Edition 2004.
Sun et al., Structure-based Design of Potent, Conformationally Constrained Smac Mimetics, 2004, J. Am. Chem. Soc. 126:16686-16687.
Srinivasula et al., A conserved XIAP-interaction motif in caspase-9 and Smac/DIABLO regulates caspase activity and apoptosis, 2001, Nature 410:112-116.
Sun et al., NMR Structure and Mutagenesis of the Third Bir Domain of the Inhibitor of Apoptosis Protein XIAP, 2000, J. Biol. Chem. 275(43):33777-33781.
Stellar, Mechanisms and Genes of Cellular Suicide, 1995, Science 267:1445-1449.
Sun et al., NMR structure and mutagenesis of the inhibitor-of-apoptosis protein XIAP, 1999, Nature 40:818-822.
Shi, Survivin structure: crystal unclear, 2000, Nat. Str. Biol. 7(8):620-623.
Srinivasula et al., Molecular Determinants of the Caspase-promoting activity of Smac/DIABLO and its role in the death receptor pathway, 2000, J. Biol. Chem. 275(46):36152-36157.
Terwilliger et al., The CCP4 suite: Programs for protein crystallography, 1994, Acta Crystallogr. D50:760-763.
Terwilliger et al., Correlated Phasing of Multiple Isomorphous Replacement Data, 1996, Acta Cnystallogr. D52:749-757.
Takahashi et al., A Single BIR Domain XIAP Sufficient for Inhibiting Caspases, 1998, J. Biol. Chem. 273(14):7787-7790.
Weinstein ed., Chemistry and Biochemistry of Amino Acids, Peptides, and Proteins, 1983, Marcel Dekker, Inc., New York, New York (TOC).

SMAC MIMETIC

CROSS-REFERENCE TO RELATED APPLICATIONS

This application is a continuation of co-pending U.S. application Ser. No. 14/607,752, filed Jan. 28, 2015, which is a continuation of U.S. application Ser. No. 14/075,190, filed Nov. 8, 2013, and issued as U.S. Pat. No. 8,986,993, which is a continuation of U.S. application Ser. No. 13/611,274, filed Sep. 12, 2012, and issued as U.S. Pat. No. 8,603,816, which is a divisional of U.S. application Ser. No. 12/819,221, filed Jun. 20, 2010, and issued as U.S. Pat. No. 8,283,372, which is a non-provisional of U.S. Application Ser. No. 61/222,668, filed Jul. 2, 2009; the entire contents of all listed applications are herein incorporated by reference.

FIELD OF THE INVENTION

This invention is in the field of SMAC mimetics and compositions and uses thereof to treat proliferative disorders including cancers.

BACKGROUND OF THE INVENTION

Inhibitors of Apoptosis Proteins (IAPB) are naturally occurring intra-cellular proteins that suppress caspase-dependent apoptosis. SMAC, also known as DIABLO, is another intracellular protein that functions to antagonize, i.e., inhibit the activity of IAPB. In normal healthy cells, SMAC and IAPB function together to maintain healthy cells. However, in certain disease states, e.g., cancers and other proliferative disorders, IAPB are not adequately antagonized and therefore prevent apoptosis and cause or exacerbate abnormal proliferation and survival.

SMAC mimetics, also known as IAP antagonists, are synthetic small molecules that mimic the structure and IAP antagonist activity of the four N-terminal amino acids of SMAC. (SMAC mimetics are sometimes referred to as IAP antagonists.) When administered to animals suffering proliferative disorders, the SMAC mimetics antagonize IAPB, causing an increase in apoptosis among abnormally proliferating cells.

Examples of SMAC peptidomimetics are those disclosed in U.S. Pat. No. 7,517,906; U.S. Pat. No. 7,309,792; U.S. Pat. No. 7,419,975; US 2005/0234042; US 2005/0261203; US 2006/0014700; US 2006/0025347; US 2006/0052311; US 2006/0128632; US 2006/0167066; US 2007/0042428; US 2007/032437; US 2008/0132485; WO 2005/069888; WO 2005/069894; WO 2006/010118; WO 2006/122408; WO 2006/017295; WO 2006/133147; WO 2006/128455; WO 2006/091972; WO 2006/020060; WO 2006/014361; WO 2006/097791; WO 2005/094818; WO 2008/045905; WO 2008/016893; WO 2007/136921; WO 2007/021825; WO 2007/130626; WO 2007/106192; and WO 2007/101347.

SUMMARY OF THE INVENTION

This invention, in one aspect, is N-{1S-[2R-(6,6'-Difluoro-3'-{4S-hydroxy-1-[2S-(2S-methylamino-propionylamino)-butyryl]-pyrrolidin-2R-ylmethyl}-1H,1'H-[2,2']biindolyl-3-ylmethyl)-4S-hydroxy-pyrrolidine-1-carbonyl]-propyl}-2S-methylamino-propionamide and pharmaceutically acceptable salts thereof, as well as various forms of such compound and salts thereof as further described herein below.

This compound has the following structure:

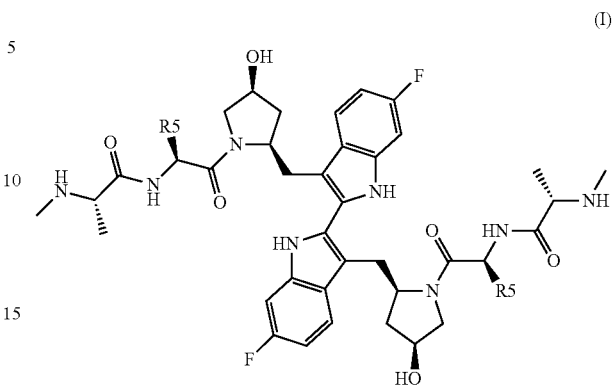

(I)

wherein R5 is —CH2CH3. This compound is also referred to herein as Compound 15.

The invention, in related aspects, comprises a pharmaceutical composition comprising such compound and a method of treating a proliferative disorder in a human or non-human mammalian subject in need thereof that comprises internally administering to the subject an effective amount of said compound or a pharmaceutically acceptable salt thereof.

In other aspects, the invention comprises a method of treating a proliferative disorder in a mammal in need thereof, e.g., a human, or a companion animal, a food animal, or a sporting animal, that comprises internally administering to the animal an effective amount of Compound 15 or a pharmaceutically acceptable salt thereof.

In another illustrative embodiment, the invention comprises a method for inducing apoptosis in a cell comprising contacting the cell with Compound 15 or a pharmaceutically acceptable salt thereof. In this embodiment, the cell can be, e.g., a cancerous cell.

In additional illustrative embodiments, the invention comprises any one or more of the above methods that further comprises administering a second cancer-related therapy, such as, e.g., radiation, chemotherapy, immunotherapy, photodynamic therapy, and combinations thereof.

In a further illustrative embodiment, the invention comprises a method of treating an autoimmune disease, in which the condition is caused or exacerbated by abnormal regulation of apoptosis, in a mammal in need thereof, including, for example, systemic lupus erythematosus, psoriasis, and idiopathic thrombocytopenic purpura (Morbus Werlhof) that comprises internally administering to the animal an effective amount of Compound 15 or a pharmaceutically acceptable salt thereof.

DETAILED DESCRIPTION OF THE INVENTION

Figure 1:
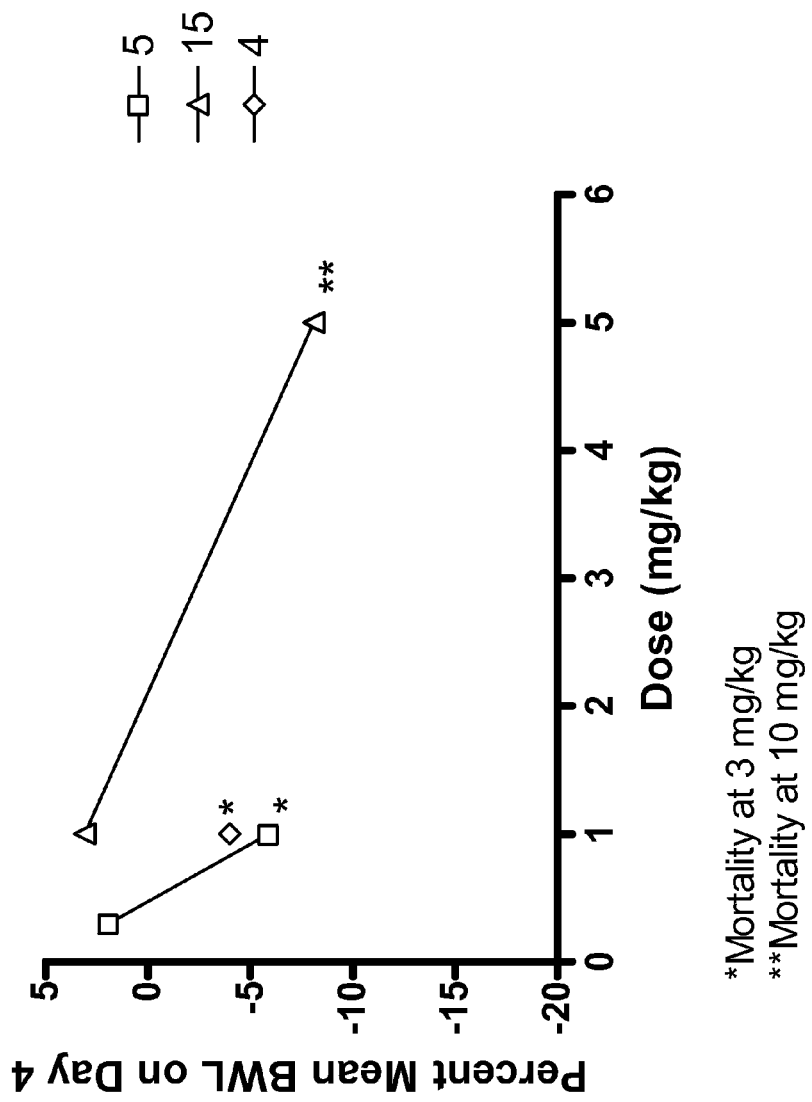
FIG. 1 shows percent mean body weight loss in rat following 4 days of intravenous bolus dosing with SMAC mimetics substantially as described in Example 4.

The compound of the invention is a SMAC mimetic that can be used in the treatment of proliferative disorders, e.g.:

various benign tumors or malignant tumors (cancer), benign proliferative diseases (e.g., psoriasis, benign prostatic hypertrophy, and restenosis), or autoimmune diseases (e.g., autoimmune proliferative glomerulonephritis, lymphoproliferative autoimmune responses). Cancers which potentially can be treated with IAP antagonists include, but are not limited to, one or more of the following: lung adenocarcinoma, pancreatic cancer, colon cancer, ovarian cancer, breast cancer, mesothelioma, peripheral neuroma, bladder cancer, glioblastoma, melanoma, adrenocortical carcinoma, AIDS-related lymphoma, anal cancer, bladder cancer, meningioma, glioma, astrocytoma, breast cancer, cervical cancer, chronic myeloproliferative disorders (e.g., chronic lymphocytic leukemia, chronic myelogenous leukemia), colon cancer, endocrine cancers, endometrial cancer, ependymoma, esophageal cancer, Ewing's sarcoma, extracranial germ cell tumors, extragonadal germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, intraocular melanoma, islet cell carcinoma, Kaposi sarcoma, laryngeal cancer, leukemia, acute lymphoblastic leukemia, acute myeloid leukemia, lip cancer, oral cavity cancer, liver cancer, male breast cancer, malignant mesothelioma, medulloblastoma, melanoma, Merkel cell carcinoma, metastatic squamous neck cancer, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, oropharyngeal cancer, bone cancers, including osteosarcoma and malignant fibrous histiocytoma of bone, ovarian epithelial cancer, ovarian germ cell tumors, ovarian low malignant potential tumors, pancreatic cancer, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, skin cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

Some embodiments of the invention include inducing apoptosis of cells, particularly pathologically proliferating cells. The methods can be carried out in vitro or in vivo.

The methods of the invention can include administration of the compound of the invention alone, administration of a combination of IAP antagonists, or administration of the compound of the invention, with or without one or more additional IAP antagonists, and one or more additional chemotherapeutic agents. Administration of multiple agents can be simultaneous or sequential. Useful chemotherapeutic agents include, but are not limited to, alkylating agents (e.g., cyclophosphamide, mechlorethamine, chlorambucil, melphalan), anthracyclines (e.g., daunorubicin, doxorubicin, epirubicin, idarubicin, mitoxantrone, valrubicin), cytoskeletal disruptors (e.g., paclitaxel, docetaxel), epothilones (e.g., epothilone A, epothilone B, epothilone D), inhibitors of topoisomerase II (e.g., etoposide, teniposide, tafluposide), nucleotide analogs precursor analogs (e.g., azacitidine, azathioprine, capecitabine, cytarabine, doxifluridine, fluorouracil, gemcitabine, mercaptopurine, methotrexate, tioguanine), peptide antibiotics (e.g., bleomycin), platinum-based agents (e.g., carboplatin, cisplatin, oxaliplatin), retinoids (e.g., all-trans retinoic acid), and vinca alkaloids and derivatives (e.g., vinblastine, vincristine, vindesine, vinorelbine). In some embodiments, chemotherapeutic agents include fludarabine, doxorubicin, paclitaxel, docetaxel, camptothecin, etoposide, topotecan, irinotecan, cisplatin, carboplatin, oxaliplatin, amsacrine, mitoxantrone, 5-fluoro-uracil, or gemcitabine.

In some embodiments of the invention, pharmaceutical compositions comprising the compound of the invention, alone or in combination with one or more other active pharmaceutical ingredients, are administered to a human or veterinary subject. The pharmaceutical compositions typically comprise at least one pharmaceutically acceptable excipient, e.g., a carrier or diluent, and can be administered in the conventional manner by routes including systemic, topical, or oral routes. Administration is normally by intravenous injection, either as a bolus or infusion, but other routes of administration are not precluded. An intravenous formulation can be 1 mg/mL of Compound 15 in sterile 0.05M citrate buffered saline, pH 5. Specific modes of administration will depend on the indication and other factors including the particular compound being administered. The amount of compound to be administered is that amount which is therapeutically effective. The dosage to be administered will depend on the characteristics of the subject being treated, e.g., the particular patient treated, age, weight, health, types of concurrent treatment, if any. Frequency of treatments can be easily determined by one of skill in the art (e.g., by the clinician).

Typically, the compound of the invention will be administered by intravenous injection, including, e.g., by infusion over about 1 to about 120 minutes, e.g., about 30 minutes.

The pharmaceutical composition of the invention is a composition in which the active pharmaceutical ingredient, i.e., the compound of the invention, is pure enough, and the composition is otherwise suitable, for internal administration to a human or other mammal. It can be prepared in unit dose form, i.e., a form suitable for single administration to a subject. So, e.g., a pharmaceutical composition in intravenous unit dose form may comprise a vial or pre-filled syringe, each comprising an effective amount or a convenient fraction of an effective amount such that one the contents of one vial or syringe are administered at a time. Such administration can be repeated up to about 4 times per day over a period of time, if necessary to achieve a cumulative effective dose, e.g., tumor regression. A dosing regimen can be, e.g., daily or twice-weekly intravenous injections, or, e.g., weekly injections in cycles of three weeks on and one week off for as long as the treatment is effective, e.g., until disease progresses or the drug is not tolerated. The effective dose administered in each injection is an amount that is effective and tolerated; it can be, e.g., 0.01 to 30 mg/m$^2$, e.g., 0.2 to 10 mg/m$^2$, or, e.g., 0.5 to 5 mg/m$^2$.

The compound of the invention can also be applied locally, such as in isolated limb perfusion. The compound of the invention can also be applied topically, e.g., as a cream, gel, lotion, or ointment, or in a reservoir or matrix-type patch, or in an active transdermal delivery system.

An effective dose is one that over the course of therapy, which may be, e.g., 1 or more weeks, e.g., multiple courses of 3 weeks on/1 week off, results in treatment of the proliferative disorder, i.e., a decrease in the rate of disease progression, termination of disease progression, or regression or remission.

Pharmaceutical compositions to be used comprise a therapeutically effective amount of a compound as described above, or a pharmaceutically acceptable salt or other form thereof together with one or more pharmaceutically acceptable excipients. The phrase "pharmaceutical composition"

refers to a composition suitable for administration in medical use. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of the compound of the invention, which is preferably isotonic with the blood of the recipient. This aqueous preparation may be formulated according to known methods using suitable carriers or diluents which may include a buffer.

When practicing the conjoint or combination therapy described in more detail below, the administration of the compound and compositions of the present invention can occur simultaneous with, subsequent to, or prior to chemotherapy or radiation, so long as the chemotherapeutic agent or radiation sensitizes the system to the compound and compositions of the present invention.

The present invention also is directed to the use of the compound and compositions as a chemopotentiating agent with other treatment approaches. The term "chemopotentiating agent" refers to an agent that acts to increase the sensitivity of an organism, tissue, or cell to a chemical compound, or treatment namely "chemotherapeutic agents" or "chemo drugs" or to radiation treatment. Thus, compound and compositions of the present invention can be used for inhibiting tumor growth in vivo by administering them in combination with a biologic or chemotherapeutic agent or by using them in combination with radiation. In these applications, the administration of the compound and compositions of the present invention may occur prior to, and with sufficient time, to cause sensitization of the site to be treated. Alternatively, the compound and compositions of the present invention may be used contemporaneously with radiation and/or additional anti-cancer chemical agents (infra). Such systems can avoid repeated administrations of the compound and compositions of the present invention, increasing convenience to the subject and the physician, and may be particularly suitable for certain compositions of the present invention.

Biological and chemotherapeutics/anti-neoplastic agents and radiation induce apoptosis by activating the extrinsic or intrinsic apoptotic pathways, and, since the compound and compositions of the present invention relieve antagonists of apoptotic proteins (IAPs) and, thus, remove the block in apoptosis, the combination of chemotherapeutics/anti-neoplastic agents and radiation with the compound and compositions of the present invention should work additively or synergistically to facilitate apoptosis.

A combination of the compound of the present invention and a biological or chemotherapeutic/anti neoplastic agent and/or radiation therapy of any type that activates the extrinsic or intrinsic pathway may provide a more effective approach to destroying tumor cells. The compound of the present invention interacts with IAP's, such as XIAP, cIAP-1, cIAP-2, ML-IAP, etc., and removes the IAP mediated block of apoptosis. Most chemotherapeutics/anti neoplastic agents and/or radiation therapy kills actively dividing cells by activating the intrinsic apoptotic pathway leading to apoptosis and cell death. Biological antitumor agents such as TRAIL (TNF-related apoptosis inducing ligand) activate extrinsic apoptotic pathways. As is described in more detail below, embodiments of the invention provide combinations of the compound of the present invention and a biological or chemotherapeutic/anti-neoplastic agent and/or radiation which provide a synergistic action against unwanted cell proliferation. This synergistic action between the compound of the present invention and a biological or chemotherapeutic/anti-neoplastic agent and/or radiation therapy can improve the efficiency of the biological or chemotherapeutic/anti-neoplastic agent and/or radiation therapies. This will allow for an increase in the effectiveness of current biological or chemotherapeutic/anti-neoplastic agents or radiation treatments allowing a higher percentage of tumors to respond to the therapy, an improved tumor response, and, potentially, a reduction in the dose of the biological or chemotherapeutic/anti-neoplastic agent needed to treat a tumor, thereby providing the use of a more tolerable dose of biological or chemotherapeutic/anti-neoplastic agent and/or radiation.

In an embodiment of the present invention, the patient is treated by administering the compound or a pharmaceutical composition of the present invention at a time the patient is subject to concurrent or antecedent radiation or chemotherapy for treatment of a neoproliferative pathology of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

In another embodiment of the present invention, the compound or a composition of the present invention can be administered in combination with a biological or chemotherapeutic and/or for use in combination with radiotherapy, immunotherapy, and/or photodynamic therapy, promoting apoptosis and enhancing the effectiveness of the chemotherapeutic, radiotherapy, immunotherapy, and/or photodynamic therapy.

Embodiments of the invention also include a method of treating a patient afflicted with cancer by the contemporaneous or concurrent administration of a biological or chemotherapeutic agent. Such biological or chemotherapeutic agents include but are not limited to the chemotherapeutic agents described in "Modern Pharmacology with Clinical Applications", Sixth Edition, Craig & Stitzel, Chpt. 56, pg 639-656 (2004), herein incorporated by reference. The chemotherapeutic agent can be, but is not limited to, alkylating agents, antimetabolites, anti-tumor antibiotics, plant-derived products such as taxanes, enzymes, hormonal agents, miscellaneous agents such as cisplatin, monoclonal antibodies, glucocorticoids, mitotic inhibitors, topoisomerase I inhibitors, topoisomerase II inhibitors, immunomodulating agents such as interferons, cellular growth factors, cytokines, and nonsteroidal anti-inflammatory compounds (NSAID), cellular growth factors and kinase inhibitors. Other suitable classifications for chemotherapeutic agents include mitotic inhibitors, and anti-estrogenic agents.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL and other members, i.e., other than TRAIL and TNF-alpha, of the TNF superfamily of molecules, interferon (in both its alpha and beta forms), thalidomide, thalidomide derivatives such as lenalidomide, melphalan, and PARP inhibitors. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim.

Another embodiment of the present invention relates to the use of the compound or a composition of the present invention in combination with topoisomerase inhibitors to potentiate their apoptotic inducing effect. Topoisomerase inhibitors inhibit DNA replication and repair, thereby promoting apoptosis and are used as chemothemotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors. Topoisomerase inhibitors of both the Type I class (camptothecin, topotecan, SN-38 (irinotecan active metabolite) and the Type II class (etoposide) are expected to show potent synergy with compounds of the present invention. Further examples of topoisomerase inhibiting agents that may be used include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

Another embodiment of the present invention relates to the use of the compound or a composition of the present invention in combination with nonsteroidal antiinflammatory drugs (NSAIDs).

In another embodiment of the invention, the chemotherapeutic/anti-neoplastic agent for use in combination with the compound and compositions of the present invention may be a platinum containing compound. In one embodiment of the invention, the platinum containing compound is cisplatin. Cisplatin can synergize with a compound of the present invention and potentiate the inhibition of an IAP, such as but not limited to XIAP, cIAP-1, c-IAP-2, ML-IAP, etc. In another embodiment a platinum containing compound is carboplatin. Carboplatin can synergize with a compound of the present invention and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a compound of the present invention and potentiate the inhibition of an IAP, including, but not limited to, XIAP, cIAP-1, c-IAP-2, ML-IAP, etc.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of cross-bridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Yet another embodiment of the present invention is the therapeutic combination or the therapeutic use in combination of the compound or compositions of the present invention with TRAIL or TRAIL agonist antibodies, or other chemical or biological agents which bind to and activate the TRAIL receptor(s). Many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, overexpression of FLIP which competes for zymogen caspase-8 binding during DISC formation and inhibition of activated caspase-3 and/or caspase-9 by XIAP. In TRAIL resistance, a compound or composition of the present invention may increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In another embodiment of the invention, Compound 15 is administered in combination with a cytokine, e.g., TNFα.

The compound and compositions of the present invention also can be used to augment radiation therapy (or radiotherapy), i.e., the medical use of ionizing radiation as part of cancer treatment to control malignant cells. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body.

Compound 15 is capable of forming pharmaceutically acceptable salts, including but not limited to acid addition and/or base addition salts. Such salts are included within all aspects of the invention.

It is intended that the present invention encompass Compound 15 synthesized in vitro using laboratory techniques, such as those well known to synthetic chemists; or synthesized using in vivo techniques, such as through metabolism, fermentation, digestion, and the like. It is also contemplated that the compound of the present invention may be synthesized using a combination of in vitro and in vivo techniques.

The present invention also includes isotopically-enriched compounds, which are identical to Compound 15 but for the fact that one or more atoms are replaced by an atom having an atomic mass or mass number different from the atomic mass or mass number usually found in nature. Examples of isotopes that can be included in the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. Substitution with heavier isotopes such as deuterium, i.e., $^{2}H$, are also included. Isotopically enriched compounds of this invention can generally be prepared by substituting a readily available isotopically labelled reagent for a non-isotopically enriched reagent. For example, incorporation of deuterium can be accomplished by substituting sodium borohydride with d4-sodium borohydride, or by replacing iodomethane with d3-iodomethane. Representative examples of specific deuterated analogs and their preparation are described in Example 1.

Compound 15 may exist in unsolvated forms as well as solvated forms, including hydrated forms. Furthermore, Compound 15 may exist in various solid states including crystalline, semi-crystalline and amorphous (noncrystalline) forms, and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these and other such forms are intended to be encompassed within the scope of the term, Compound 15.

References to Compound 15 and to the compound of the invention, and other similar phrases in this specification and in the claims, are intended to include not only the compound of formula (I), but also pharmaceutically acceptable salts of Compound 15, as well as various forms of said compound or salts thereof such as those that are described above and below.

In additional embodiments, the invention comprises compounds useful as intermediates in the synthesis of Compound 15, as well as in processes for preparing such intermediates and Compound 15. For example, in such embodiments, the invention comprises compounds shown in the Examples, below, such as Compounds 9, 10, 11, 12, 13, 14, and the isotopically enriched compounds such as Compounds 18 through 32. One such embodiment is Compound 15 in which the 4-OH substituent on the pyrrolidine moiety is protected with a protecting group. An illustrative protecting group is an acetyl group, which is illustrated in Compounds 11-14, below. Other useful protecting groups will be apparent to persons of skill in the art and include, e.g., benzoyl, benzyl, trimethylsilyl, and triphenylmethyl groups. The protecting group is removed, e.g., by contacting the protected intermediate with an acid or a base, as shown in Schemes XIII and XIV, below. Thus, the invention comprises the compound having the structure of Compound 15 as well as protected versions of Compound 15 such as Compounds 13 and 14 in which the N-termini are protected with carbamate moieties and/or free hydroxyl groups are protected as esters such compounds being herein referred to as Protected Compound 15. The invention further comprises the step of deprotecting a Protected Compound 15 by contacting the Protected Compound 15 with an acid or base whereby the Protecting Group is removed to afford Compound 15. Isotopically enriched compounds of the invention include deuterated forms of Compound 15 such as Compounds 20, 29, and 32. Protected forms of such compounds, e.g., Compounds 19, 28, and 31, are also comprised within the invention.

EXAMPLES

The following preparations and schemes are illustrative of synthesis of compounds of the present invention. Abbreviations which are used throughout these schemes and in the application generally, are identified in the following table:

| ABBREVIATION | MEANING |
|---|---|
| ACN | Acetonitrile |
| Ac₂O | Acetic anhydride |
| Cbz and Z | Benzyloxycarbonyl |
| Boc and/or boc | tert-butyloxycarbonyl |
| THF | Tetrahydrofuran |
| DCM | Dichloromethane |
| DDQ | 2,3-dichloro-5,6-dicyano-1,4-benzoquinone |
| mCPBA | 3-chloroperbenzoic acid |
| Cbz-Cl | Benzyloxycarbonyl chloride |
| Hex | Hexanes |
| HPLC | high performance liquid chromatography |
| TLC | thin layer chromatography |
| EtOAc | ethyl acetate |
| Ph | Phenyl |
| HATU | 2-(7-Aza-1H-benzotriazole-1-yl)-1,1,3,3-tetramethyluronium hexafluorophosphate |
| Me | Methyl* |
| iPr | Iso-propyl |
| cPr | Cyclopropyl |
| NMP | N-methylpyrrolidinone |
| PhCOCl | Benzoyl chloride |
| DIAD | diisopropyl azo dicarboxylate |
| DIBAL | Diisobutylaluminium hydride |
| DMAP | 4-dimethylamino pyridine |
| DMF | Dimethylformamide |
| DMSO | dimethyl sulfoxide |
| TFA | trifluoroacetic acid |
| TFAA | trifluoroactic anhydride |
| HOAc or AcOH | acetic acid |
| DIPEA | Diisopropylethylamine |
| NMM | N-methylmorpholine |
| NCS | N-chlorosuccinimide |
| TEA (Et₃N) | Triethylamine |
| MsCl | Methane-sulfonylchloride |
| Et | Ethyl |
| tBu or tert-Bu | tert-butyl |
| cHex | Cyclohexyl |
| (2R—EtOMe) and/or R—MeCHOMe | Me—CH(OMe)—Me structure |
| TBAF | tetrabutyl ammonium fluoride |
| OMs | Methanesulfonyloxy |
| TBDMSCl or TBSCl | tert-butyl-dimethyl-silyl chloride |
| Ph₃P | Triphenylphosphine |
| n-Bu | Normal butyl |
| Swern[O] | Swern Oxidation |
| TBA-Cl | Tetra-n-butyl ammonium chloride |
| NP-HPLC | Normal phase-high performance liquid chromatography |
| EDCI | N-3-(dimethylaminopropyl)-N'-ethylcarbodiimide hydrochloride 1-Ethyl-3-(3-Dimethylaminopropyl)carbodiimide-HCl |
| Et₂O | Ethylene oxide (epoxide structure) |
| TES | Triethylsilane |
| MeNO₂ | Nitromethane |
| EtOH | Ethanol |
| DCE, or EDC | Dichloroethane, Ethylenedichloride |
| NaHMDS | Sodium hexamethyldisilazide or sodium bis(trimethylsilyl)amide |
| (2R—EtOH) and/or R—MeCHOH | Me—CH(OH)—Me structure |
| MsCl | Methanesulfonyl chloride |
| OTs | —O—SO₂—Ph—Me |
| OTBS | tert-butyl-dimethyl-silanyloxy |

-continued

| ABBREVIATION | MEANING |
|---|---|
| Ac | Acetyl |
| DMA | Dimethylamine |
| HWE | Honer-Wadsworth-Emmons reaction |
| DMS | Dimethylsulfide |
| Meldrum's Acid | 2,2-dimethyl-1,3-dioxane-4,6-dione |
| Imid. | Imidazole |
| HOBT, or HBT | Hydroxybenzotriazole |
| RT | Room temperature |
| MeOH | Methanol |
| NaOAc | Sodium acetate |
| ClCO$_2$Me | Ethyl chloroformate |
| TBSCl | tert-butyl-dimethyl-silanyl chloride |
| Boc-Chg-OH (Boc-L-cyclohexylglcine) | |
| Boc—N(Me)Ala-OH | |
| Boc-Abu-OH | |
| Boc-Ser-OH | |
| Boc-Ser(Me)-OH | |
| Boc-Thr(tBu)-OH | |
| Boc-Thr(Me)-OH | |
| h | hour |

-continued

| ABBREVIATION | MEANING |
|---|---|
| Cbz-N(Me)Ala-OH Z-N(Me)Ala-OH | |
| Boc-Tle-OH | |
| Boc-Val-OH | |
| Cbz-Ser(tBu)-OH | |
| Cbz-Thr(tBu)-OH | |
| Boc-Thr-OH | |
| PSI | Pounds per Square Inch (Gauge) |
| NaOMe | Sodium methoxide |

Example 1—Synthesis

Scheme I

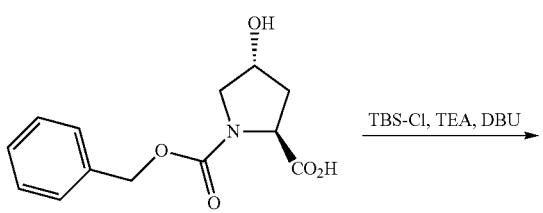

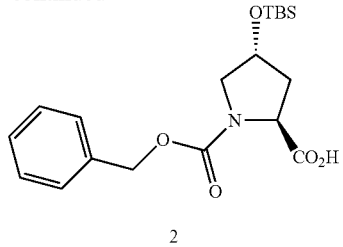

2

4-(tert-Butyl-dimethyl-silanyloxy)-pyrrolidine-1,2-dicarboxylic acid 1-benzyl ester (2)

A solution of Z-Hyp-OH (1, 300 g, 1.13 mol), TEA (395 mL, 2.83 mol), and DBU (17.2 g, 1.13 mol) in DMF (1.25 L) was stirred in a cold water bath while a suspension of TBS-Cl (188 g, 1.24 mol) in DMF (270 mL) was added slowly at 21-26° C. [Note: moderately exothermic]. The resulting thin suspension was stirred for 22 h at ambient temperature. The reaction mixture was cooled to 2° C. and quenched with water (1.54 L) at ≤26° C. [Note: the pH of the aqueous layer was 8.5-9.0]. MTBE (3 L) was added and the mixture was acidified to pH 3-4 with conc. HCl (168 g) at 17-19° C. The organic layer was separated and washed with water (2×1.5 L). The organic layer was concentrated in vacuo and dried by additional MTBE distillation. Toluene (2×500 mL) was added and distilled to remove moisture to provide 603 g of 2 as a light yellow-colored oil [Note: the water content by KF analysis was 508 ppm]. Based on drying a small sample of 2 to a solid, the contained weight of 2 was 412 g (96% yield, not corrected for purity). $^1$H NMR (300 MHz, CDCl$_3$): δ7.34 (m, 3H), 7.29 (m, 2H), 5.24-5.11 (m, 2H), 4.52 (m, 1H), 4.43 (m, 1H), 3.64-3.42 (m, 2H), 2.27-2.09 (m, 2H), 0.85 (s, 9H), 0.06 (s, 3H), 0.04 (s, 3H) ppm; $^{13}$C NMR (75 MHz, d$_6$-DMSO), mixture of rotamers: δ178.7, 178.4, 159.3, 158.9, 141.9, 141.8, 133.4, 133.3, 132.8, 132.6, 132.3, 131.9, 75.3, 74.6, 71.0, 71.0, 62.8, 62.3, 60.1, 59.7, 44.4, 43.4, 30.6, 30.6, 22.6, 22.6, 0.1, 0.0 ppm. Mass spectrum (ESI), m/z 379.5 [(M)+; calcd for C$_{19}$H$_{29}$NO$_5$Si: 379.5].

4-(tert-Butyl-dimethyl-silanyloxy)-2-(6-fluoro-1H-indole-3-carbonyl)-pyrrolidine-1-carboxylic acid benzyl ester (3)

Z-Hyp(OTBS)-OH (2, 55.5 g, 145 mmol) was dissolved in toluene (265 mL). DMF (0.1 mL) and oxalyl chloride (22.4 g, 174 mmol) were added at ambient temperature. After 2-3 h, the bubbling stopped. After 4 h, the mixture was concentrated in vacuo (65° C. bath, ca. 30 min) to provide 95 g of a light yellow-colored solution which was confirmed to be acid chloride by $^1$H NMR analysis.

6-Fluoroindole (39.2 g, 290 mmol) was dissolved in anhydrous chlorobenzene (300 mL) and toluene (200 mL) and the solution was cooled to −4° C. using an ice/acetone bath. A solution of 3M EtMgBr in diethyl ether (101 g, 294 mmol) was added over 31 minutes at ≤2.5° C. resulting in a pale amber-colored solution. After 30 min, the acid chloride/toluene solution (vide supra) was added over 45 minutes at <2° C. The reaction mixture was kept cold for 1 h then allowed to slowly warm. After ca. 4 h (10.6° C.), the reaction mixture was quenched with glacial HOAc (9.0 g, exothermic to 17.5° C.) and then water (exothermic). Water (200 mL) and EtOAc (300 mL) were added and the organic layer was separated and washed with water (100 mL, slow separation). The organic layer was concentrated in vacuo to afford 227 g of 3 as an amber-colored oil which was used without further purification. $^1$H NMR (300 MHz, CDCl$_3$), ~2:1 mixture of rotamers: δ9.38 (m, 0.7H), 8.58 (m, 0.3H), 8.35 (app. dd, J=5.2, 8.2 Hz, 0.3H), 8.03 (app. dd, J=5.2, 8.2 Hz, 0.7H), 7.74 (d, J=2.9 Hz, 0.7H), 7.66 (d, J=2.9 Hz, 0.3H), 7.38-7.32 (m, 5H), 7.07 (m, 1H), 6.95 (m, 1H), 6.85 (m, 1H), 5.26-4.92 (m, 3H), 4.54 (m, 1H), 3.80 (app. dt, J=5.2, 11.1 Hz, 1H), 3.61 (app. d, J=11.1 Hz, 0.3H), 3.55 (app. d, J=11.1 Hz, 0.7H), 2.25-2.07 (m, 2H), 0.88 (s, 9H), 0.06 (s, 3H), 0.00 (s, 3H) ppm; $^{13}$C NMR (75 MHz, d$_6$-DMSO), mixture of rotamers: δ193.4, 193.0, 159.3 (d, J$_{CF}$=235.5 Hz), 153.9 (d, J$_{CF}$=16.2 Hz), 136.7, 136.8 (d, J$_{CF}$=34.0 Hz), 134.6, 128.3, 127.8, 127.2, 126.6, 122.4, 113.7 (d, J$_{CF}$=13.5 Hz), 110.2 (d, J$_{CF}$=20.2 Hz), 98.5 (d, J$_{CF}$=25.4 Hz), 70.6, 69.8, 65.8, 65.8, 60.6, 60.3, 55.5, 55.0, 25.7, 25.6, 17.7, 17.7, −4.8, −4.9 ppm. Mass spectrum (ESI), m/z 518.9 [[(M−H)+Na]+; calcd for C$_{27}$H$_{32}$FN$_2$O$_4$SiNa: 518.6].

Scheme II

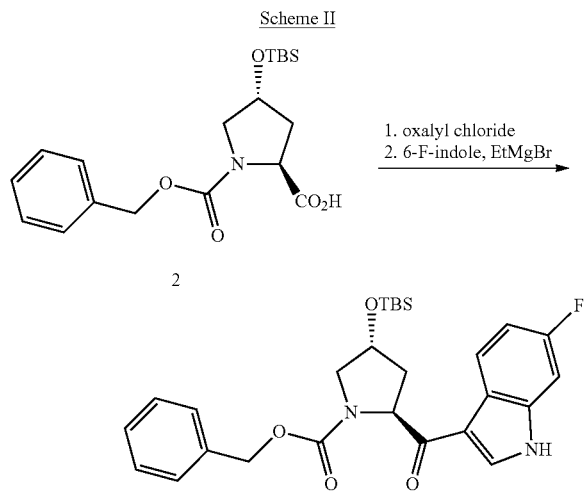

Scheme III

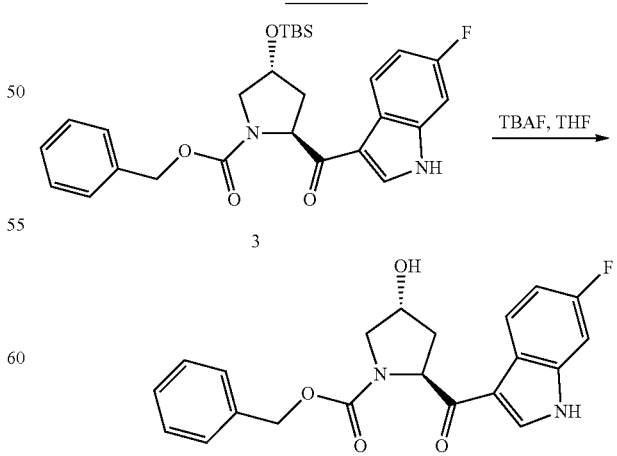

2-(6-Fluoro-1H-indole-3-carbonyl)-4-hydroxy-pyrrolidine-1-carboxylic acid benzyl ester (4)

To a solution containing 3 (227 g) in THF (600 mL) was added 1 M TBAF in THF (160 mL) at ambient temperature. After 9 h, another 20 mL of the 1 M TBAF/THF solution was added. After ca. 48 h, the reaction mixture was concentrated in vacuo and then redissolved in EtOAc (600 mL). The organic solution was washed with water (310 mL) and the product precipitated to form a thick suspension which was filtered (slow). The solids were washed with EtOAc (165 mL in portions) and dried to provide 43 g of 4. The combined filtrate was concentrated in vacuo to precipitate an additional 4.8 g of 4 after drying. $^1$H NMR (300 MHz, $d_6$-DMSO), mixture of rotomers: δ12.08 (br s, 1H), 8.43 (d, J=10.5 Hz, 1H), 8.16 (ddd, J=5.4, 8.7, 14.1 Hz, 1H), 7.36-7.31 (m, 2H), 7.27 (app. d, J=10.2 Hz, 1H), 7.09-6.93 (m, 4H), 5.24 (dt, J=8.1, 15.6 Hz, 1H), 5.14 (br s, 1H), 5.04 (app. d, J=6.4 Hz, 1H), 4.90 (app. dd, J=13.4, 28.4 Hz, 1H), 4.30 (br s, 1H), 3.58-3.43 (m, 2H), 2.27 (m, 1H), 1.93 (m, 1H) ppm; $^{13}$C NMR (75 MHz, $d_6$-DMSO), mixture of rotomers: δ194.0, 193.6, 159.9 (d, $J_{CF}$=235.2 Hz), 154.6 (d, $J_{CF}$=9.6 Hz), 138.1. 137.5 (d, $J_{CF}$=26.9 Hz), 136.0, 129.0, 128.5, 128.1 (d, $J_{CF}$=40.0 Hz), 123.4, 123.3, 123.0, 122.9, 114.4 (d, $J_{CF}$=11.7 Hz), 110.6 (d, $J_{CF}$=23.7 Hz), 99.3 (d, $J_{CF}$=25.2 Hz), 69.5, 68.8, 66.4, 66.3, 61.4, 61.1, 56.2, 55.7 ppm. Mass spectrum (ESI), m/z 382.6 [(M)+; calcd for $C_{21}H_{19}FN_2O_4$: 382.3].

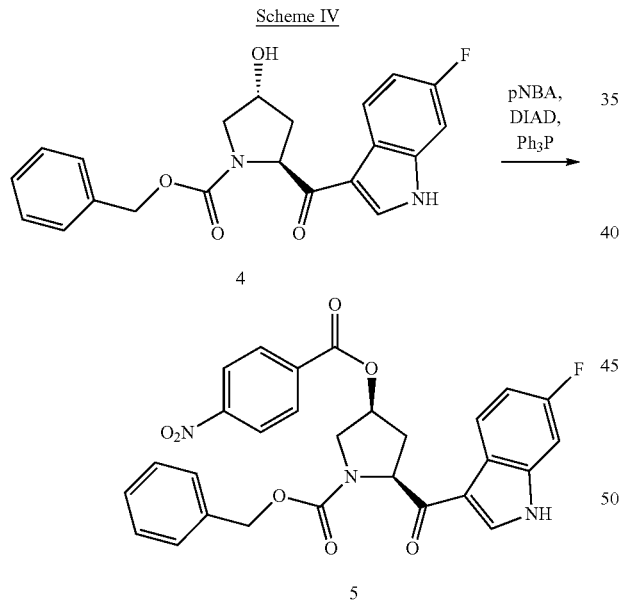

2-(6-Fluoro-1H-indole-3-carbonyl)-4-(4-nitro-benzoyloxy)-pyrrolidine-1-carboxylic acid benzyl ester (5)

A solution containing 4 (51.1 g, 134 mmol), 4-nitrobenzoic acid (27.9 g, 167 mmol) and triphenylphosphine (48.9 g, 187 mmol) in anhydrous THF (700 mL) and DMF (175 mL) was cooled to 2° C. DIAD (37.4 mL, 194 mmol) was added over 1 h at 2-3° C. After 1 h, the solution was allowed to warm to ambient temperature. After ca. 16 h, the reaction mixture was concentrated in vacuo and MeOH (250 mL) was added and concentrated to form a thick suspension (322 g). Additional MeOH (250 mL) was added and the solution was concentrated in vacuo to afford a thick suspension (420 g) that was chilled in an ice bath. After ca. 1.5 h, the solid was collected on a vacuum filter and washed with chilled MeOH (190 mL). The product was air-dried on the filter to provide 82.9 g (>100%) of 5 as a light yellow-colored solid which was used directly in the next reaction. $^1$H NMR (300 MHz, $d_6$-DMSO), mixture of rotomers: δ12.14 (br s, 1H), 8.47 (app. d, J=6.6 Hz, 1H), 8.29-8.21 (m, 3H), 8.03 (dd, J=2.7, 8.4 Hz, 2H), 7.43-7.33 (m, 2H), 7.28 (app. dd, J=2.1, 9.6 Hz, 1H), 7.20-7.08 (m, 4H), 5.55 (br s, 1H), 5.42 (dd, J=8.4, 15.3 Hz, 1H), 5.13 (dd, J=12.6, 22.2 Hz, 1H), 5.04 (s, 1H), 3.99 (m, 1H), 3.73 (d, J=12.3 Hz, 1H), 2.91 (m, 1H), 2.36 (m, 1H) ppm; $^{13}$C NMR (75 MHz, $d_6$-DMSO), mixture of rotomers: δ192.9, 192.4, 164.2, 160.0 (d, $J_{CF}$=235.5 Hz), 154.5 (d, $J_{CF}$=12.0 Hz), 150.9, 137.5, 137.1 (d, $J_{CF}$=12.6 Hz), 135.6, 135.1, 131.3, 128.9 (d, $J_{CF}$=28.0 Hz), 128.5, 128.2, 128.1, 127.6, 124.2, 123.0, 113.5 (d, $J_{CF}$=8.5 Hz), 110.9 (d, $J_{CF}$=21.9 Hz), 99.1 (d, $J_{CF}$=25.5 Hz), 75.2, 74.3, 66.7, 66.5, 62.4, 62.1, 53.6, 53.0, 38.6, 37.6 ppm. Mass spectrum (ESI), m/z 531.8 [(M)+; calcd for $C_{28}H_{22}FN_3O_7$: 531.5].

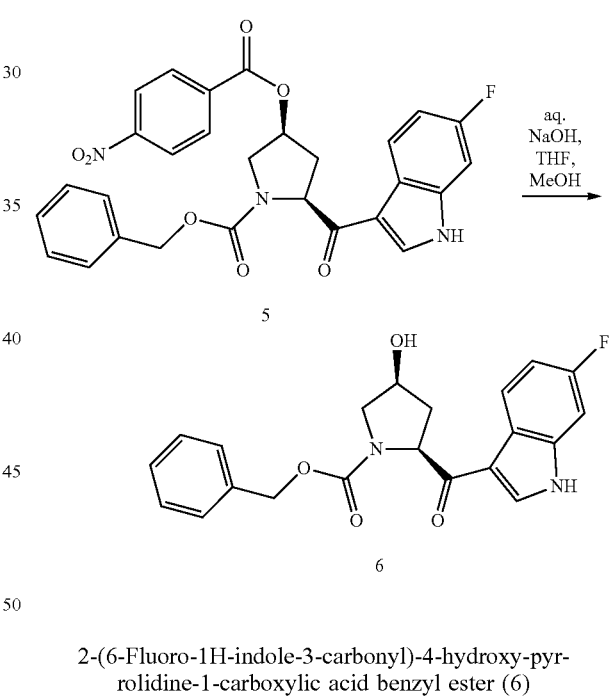

2-(6-Fluoro-1H-indole-3-carbonyl)-4-hydroxy-pyrrolidine-1-carboxylic acid benzyl ester (6)

To a suspension of 5 (82.9 g) in THF (600 mL), MeOH (200 mL), and water (100 mL) was added 50% aq. NaOH (16.0 g, 200 mmol) [Note: exothermic; temp. increase: 23.7° C. to 25.9° C.]. After 2 h, glacial HOAc (5.3 g) was added to adjust the pH to 7-8 [Note: the orange-colored solution changed to pale yellow] and the reaction mixture was concentrated in vacuo. Water (500 mL) was added and solvent was removed in vacuo until a thick suspension formed. The solid was collected on a vacuum filter and washed with water (400 mL in portions). The solid was dried in a vacuum oven at 55° C. to afford 42.6 g (83%, 2 steps) of 6 as an off-white solid. $^1$H NMR (300 MHz, $d_6$-DMSO): δ8.38 (d, J=11.1 Hz, 1H), 8.14 (ddd, J=5.7, 8.7, 14.1 Hz, 1H), 7.35-7.29 (m, 2H), 7.25 (app. dd, J=2.1, 9.9 Hz, 1H), 7.10-6.95 (m, 4H), 5.16-4.98 (m, 2H), 4.90 (app. q, J=13.5, 25.8 Hz, 1H), 4.26 (m, 1H), 3.74 (app. ddd, J=6.3, 11.1, 18.3 Hz, 1H), 3.22 (m, 1H), 2.59 (m, 1H), 1.73 (app. ddd, J=6.6, 12.9, 25.2 Hz, 1H) ppm; $^{13}$C NMR (75 MHz, d$_6$-DMSO): δ193.8, 193.3, 160.0 (d, $J_{CF}$=235.2 Hz), 154.4 (d, $J_{CF}$=14.5 Hz), 137.5 (d, $J_{CF}$=26.0 Hz), 137.2 (d, $J_{CF}$=12.3 Hz), 129.0, 128.5, 128.2 (d, $J_{CF}$=35.4 Hz), 128.1, 127.4, 123.2, 123.1, 114.4 (d, $J_{CF}$=11.4 Hz), 110.8 (d, $J_{CF}$=23.7 Hz), 110.8 (d, $J_{CF}$=23.7 Hz), 99.0 (d, $J_{CF}$=25.8 Hz), 69.4, 68.6, 66.5, 66.4, 61.5, 61.2, 54.9, 54.6 ppm. Mass spectrum (ESI), m/z 383.8 [(M+H)+; calcd for C$_{21}$H$_{20}$FN$_2$O$_4$: 383.3].

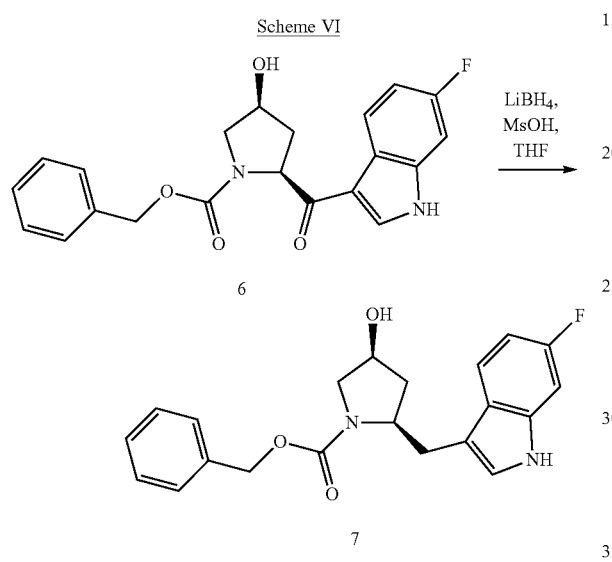

2-(6-Fluoro-1H-indol-3-ylmethyl)-4-hydroxy-pyrrolidine-1-carboxylic acid benzyl ester (7)

To a suspension of 6 (10.1 g, 26 mmol) in anhydrous THF (200 mL) was added 2M LiBH$_4$ in THF (26.2 mL, 52 mmol) over ca. 7 min [Note: exothermic; temp. increase: 21.5° C. to 28.2° C.]. After 2.5 h, the pale, yellow-colored solution was cooled to ca. 11° C. and methanesulfonic acid (4.66 g, 48 mmol) was added over ca. 4 min [Note: exothermic; temp. increase to 14.2° C.].

After 16 h, the reaction mixture was cooled in an ice-bath and carefully quenched with water (50 mL) [Note: the addition of water was exothermic and released a large quantity of gas]. Following the addition of water, the pH was adjusted to 1 with conc. HCl (1.9 g). The reaction mixture was concentrated to remove THF and the aqueous solution was extracted with EtOAc (110 mL). The organic layer was separated and washed with water (2×50 mL) [Note: final pH about 5]. The organic solution was concentrated in vacuo and azeotropically dried using anhydrous EtOAc to provide 10.2 g of 7 as a white foam [Note: 87.7 A % by HPLC analysis]. $^1$H NMR (300 MHz, d$_6$-DMSO), ~1:1 mixture of rotamers: δ10.91 (app. d, J=5.4 Hz, 1H), 7.69 (dd, J=6.0, 8.4 Hz, 0.5H), 7.48-7.30 (m, 4.5H), 7.13-7.07 (m, 3H), 6.85 (app. t, J=8.4 Hz, 0.5H), 6.58 (app. t, J=9.9 Hz, 0.5H), 5.19-5.10 (m, 3H), 4.25 (m, 1H), 4.03-3.96 (m, 1H), 3.55 (dd, J=5.1, 11.4 Hz, 1H), 3.29 (d, J=11.4 Hz, 1H), 3.17-2.98 (m, 2H), 1.79 (m, 2H) ppm. $^{13}$C NMR (300 MHz, d$_6$-DMSO), mixture of rotamers: δ159.5 (d, $J_{CF}$=232.1 Hz), 159.4 (d, $J_{CF}$=232.3 Hz), 154.9, 137.7 (d, $J_{CF}$=36.6 Hz), 136.7 (d, $J_{CF}$=12.6 Hz), 136.6 (d, $J_{CF}$=12.9 Hz), 129.1, 129.1, 128.7, 128.6 (d, $J_{CF}$=26.3 Hz), 128.2, 125.0 (d, $J_{CF}$=21.4 Hz), 124.5, 124.3, 120.1 (d, $J_{CF}$=28.3 Hz), 120.0 (d, $J_{CF}$=28.6 Hz), 112.4 (d, $J_{CF}$=14.6 Hz), 107.4 (d, $J_{CF}$=24.3 Hz), 107.3 (d, $J_{CF}$=24.3 Hz), 69.9, 69.2, 67.1, 66.3, 58.7, 58.1, 56.1, 55.6, 38.3, 37.6, 31.2, 30.1 ppm. Mass spectrum (ESI), m/z 368.6 [(M)+; calcd for C$_{21}$H$_{21}$FN$_2$O$_3$: 368.4].

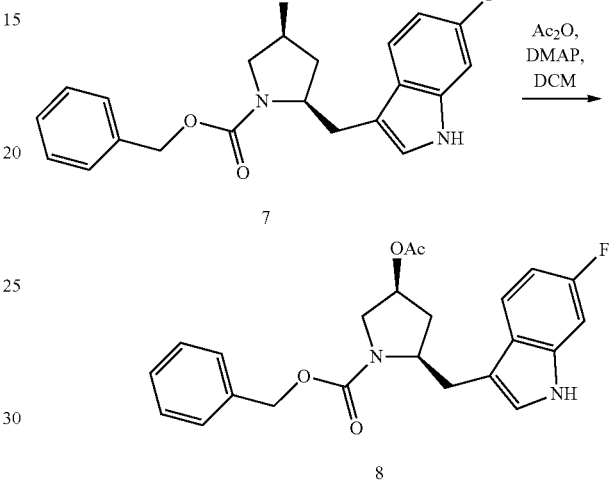

4-Acetoxy-2-(6-fluoro-1H-indol-3-ylmethyl)-pyrrolidine-1-carboxylic acid benzyl ester (8)

To a solution containing 7 (4.7 g, 12.8 mmol) and DMAP (81 mg, 0.66 mmol) in DCM (100 mL) was added acetic anhydride (2.6 g, 25.5 mmol) at ambient temperature. After 16 h, the reaction mixture was quenched with a MeOH (ca. 3 mL) and washed successively with 10% aq. Na$_2$CO$_3$ (50 mL), dilute HCl (50 mL), and 10% aq. Na$_2$CO$_3$ (50 mL). The organic solution was concentrated in vacuo and filtered through a short column of silica gel (ca. 25 g) [eluant: DCM (200 mL) to 0.5% (v/v) MeOH/DCM (80 mL) to 2% MeOH/DCM (100 mL) to 5% MeOH/DCM (100 mL)]. The product-containing fractions were combined and concentrated to provide 3.28 g (63%) of 8 as a white foam [Note: 94.3 A % by HPLC analysis]. $^1$H NMR (300 MHz, CDCl$_3$), ~1:1 mixture of rotamers: δ7.99 (m, 1H), 7.75-6.61 (m, 9H), 5.28 (m, 1H), 5.20 (m, 2H), 4.23 (m, 1H), 3.82 (dt, J=5.4, 13.5 Hz, 1H), 3.60 (app. t, J=13.2 Hz, 1H), 3.50 (d, J=11.7 Hz, 0.5H), 3.31 (d, J=12.9 Hz, 0.5H), 2.87 (dt, J=5.1, 13.5 Hz, 1H), 2.13 (s, 3H), 2.01 (m, 2H) ppm; $^{13}$C NMR (75 MHz, CDCl$_3$), ~1:1 mixture of rotamers: δ170.8, 160.2 ($J_{CF}$=236.4 Hz), 155.2, 136.8, 136.6, 136.4, 128.9, 128.8, 128.5 ($J_{CF}$=24.3 Hz), 124.5 ($J_{CF}$=21.4 Hz), 123.0, 123.0, 120.0 ($J_{CF}$=27.1 Hz), 119.9 ($J_{CF}$=26.0 Hz), 112.8 ($J_{CF}$=10.5 Hz), 108.2 ($J_{CF}$=24.3 Hz), 97.7 ($J_{CF}$=25.7 Hz), 74.0, 73.2, 67.9, 67.2, 58.5, 57.6, 53.4, 53.0, 35.4, 34.6, 30.8, 29.7, 21.5 ppm. Mass spectrum (ESI), m/z 410.6 [(M)+; calcd for C$_{23}$H$_{23}$FN$_2$O$_4$: 410.4].

Scheme VIII

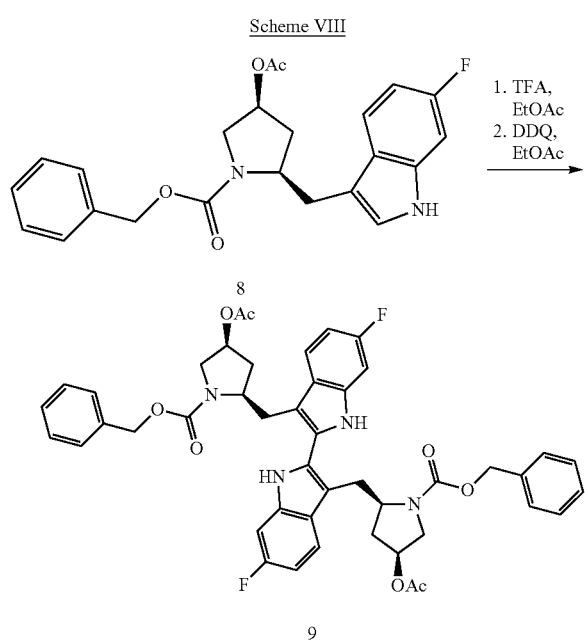

4-Acetoxy-2-[3'-(4-acetoxy-1-benzyloxycarbonyl-pyrrolidin-2-ylmethyl)-6,6'-difluoro-1H,1'H-[2,2']biindolyl-3-ylmethyl]-pyrrolidine-1-carboxylic acid benzyl ester (9)

A solution containing 8 (2.9 g, 7.1 mmol) in EtOAc (ca. 5 mL) was cooled in an ice-bath and pre-cooled TFA (20.3 mL) was added in one portion. The resulting yellow-colored solution was stirred at 2-4° C. After 4.75 h, the cold reaction mixture was transferred (via canula) with stirring into a pre-cooled mixture of EtOAc (30 mL), and 25% aq. $K_2CO_3$ (80.7 g). The aqueous layer was separated and extracted with EtOAc (3×30 mL) and the combined organic extracts were washed with 10% aq. $Na_2CO_3$ (30 g). The organic solution was concentrated in vacuo and azeotropically dried using anhydrous EtOAc to afford 2.95 g of indolylindoline diastereomers as a yellow-colored foam which was used directly in the next reaction. Mass spectrum (ESI), m/z 821.3 [(M)+; calcd for $C_{46}H_{46}F_2N_4O_8$: 820.9].

To a solution containing the indolylindoline diastereomers (2.95 g) in EtOAc (30 mL) was added DDQ (885 mg, 3.9 mmol) in one portion [Note: exothermic; temp. increase: 26° C. to 31.6° C.]. After 3 h, the dark orange/brown-colored reaction mixture was filtered through Celite® which was subsequently rinsed with EtOAc (50 mL). [Note: a second reaction performed at 0.5 mmol-scale was combined for work-up]. The filtrate was washed with 10% aq. $Na_2CO_3$ (2 washes: 74 g, then 58 g). The organic layer was concentrated in vacuo to provide 2.14 g of 9 as a light brown-colored solid.

The Celite® pad was further rinsed with THF (100 mL) which was concentrated in vacuo to provide another 1.12 g of 9 as a beige-colored solid. The combined solids were dissolved in isopropyl acetate (iPrAc, 50 mL). The iPrAc solution was reduced to ca. 20 mL and resulting suspension was warmed to reflux, cooled to ambient temperature, and then placed in an ice-bath. After 1 h, the solid was collected by vacuum filtration, washed with iPrAc (10 mL) and dried in a vacuum oven to afford 2.13 g (65%, 2 steps) of 9 as a beige-colored solid [Note: ~100 A % by HPLC analysis]. $^1$H NMR (300 MHz, $CDCl_3$): δ11.29 (br s, 2H), 7.57-7.36 (m, 14H), 6.90 (app. dt, J=2.1, 9.3 Hz, 2H), 5.39-5.30 (m, 6H), 4.28 (t, J=9.0 Hz, 2H), 3.84-3.73 (m, 4H), 3.66 (d, J=13.2 Hz, 2H), 3.40 (dd, J=12.0, 14.4 Hz, 2H), 2.31 (s, 6H), 2.17 (m, 2H), 2.05 (m, 2H) ppm; $^{13}$C NMR (75 MHz, $CDCl_3$): δ170.7, 161.9, 158.8, 156.3, 137.5, 137.3, 136.5, 128.9, 128.6, 128.5, 125.9, 118.8, 118.6, 108.8, 108.5, 108.3, 98.7, 98.3, 74.4, 68.0, 60.1, 53.5, 34.5, 28.9, 21.7 ppm. Mass spectrum (ESI), m/z 818.2 [(M)+; calcd for $C_{46}H_{44}F_2N_4O_8$: 818.8].

Scheme IX

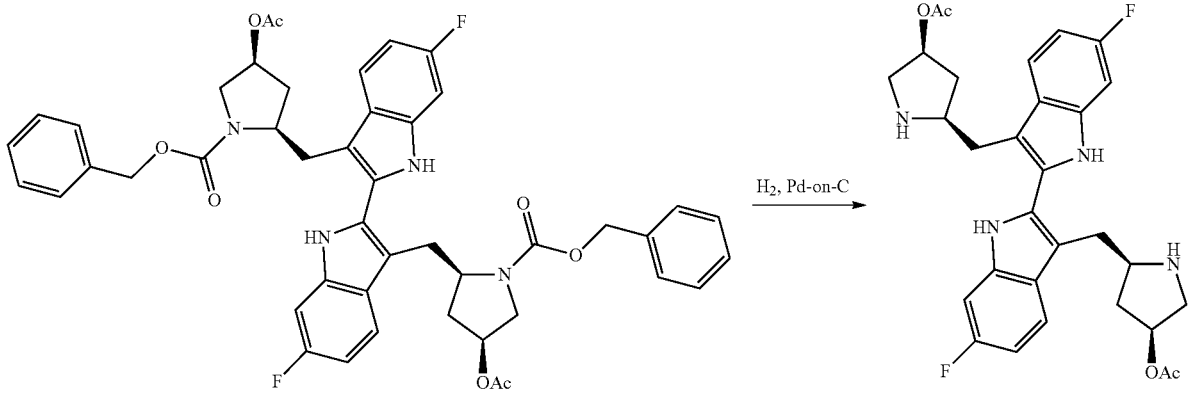

Acetic acid 5-[3'-(4-acetoxy-pyrrolidin-2-ylmethyl)-6,6'-difluoro-1H,1'H-[2,2']biindolyl-3-ylmethyl]-pyrrolidin-3-yl ester (10)

A suspension containing 9 (35 g, 42.7 mmol) in 1:1 EtOAc/MeOH (400 mL) was distributed into two 500 mL Parr bottles (ca. 200 mL/each), and charged with 10% Pd-on-C (wet, 5000 mg/each, Aldrich®). The reaction mixture was pressurized to 50 PSI $H_2$ and shaken for 3 h. The reaction mixture was filtered through a pad of Celite® and the solids were washed with EtOAc. The clarified filtrate was concentrated in vacuo to afford 24 g of 10 as an off-white solid which was used directly in the next reaction. ¹H NMR (300 MHz, CDCl₃): δ13.10 (br s, 2H) 7.45 (dd, J=5.2, 8.9 Hz, 2H), 7.03 (dd, J=2.3, 9.8 Hz, 2H), 6.85 (m, 2H), 5.35 (m, 2H), 3.71 (m, 2H), 3.18-3.35 (m, 4H), 2.90-3.14 (m, 4H), 2.56 (m, 2H), 2.00-2.10 (m, 2H), 2.04 (s, 6H), 1.80-1.92 (m, 2H) ppm; ¹³C NMR (75 MHz, CDCl₃): δ171.3, 161.7, 158.6, 136.1, 135.9, 130.5, 130.4, 125.4, 119.1, 118.9, 109.6, 108.0, 107.6, 97.6, 97.5, 75.1, 57.7, 51.6, 38.7, 32.8, 21.6 ppm. Mass spectrum (ESI), m/z 550.9 [(M)+; calcd for C₃₀H₃₂F₂N₄O₄: 550.6].

Acetic acid 5-{3'-[4-acetoxy-1-(2-tert-butoxycarbonylamino-butyryl)-pyrrolidin-2-ylmethyl]-6,6'-difluoro-1H,1'H-[2,2']biindolyl-3-ylmethyl}-1-(2-tert-butoxycarbonylamino-butyryl)-pyrrolidin-3-yl ester (11)

To a solution containing Boc-Abu-OH (20.4 g, 100 mmol) and HATU (42.0 g, 110 mmol) in anhydrous NMP (150 mL) at 0° C. was added NMM (16 mL, 150 mmol) followed by a solution of 10 (24 g, 42 mmol) in NMP (100 mL). The reaction mixture was slowly warmed to ambient temperature. After 16 h, the reaction mixture was diluted with MTBE (1000 mL) and the heterogeneous mixture was washed with water (500 mL). The layers were separated and the organic phase formed a heterogeneous suspension. MTBE (1000 mL) and EtOAc (500 mL) were added and the now-homogeneous solution was washed successively with 1 N HCl (2×100 mL), saturated aqueous NaHCO₃ (2×100 mL), brine, dried over anhydrous Na₂SO₄, filtered, and concentrated. The residue was dissolved in 1:1 DCM/MeOH (600 mL) and DCM (ca. 200 mL) was removed via distillation at 50° C. [Note: a small quantity of white precipitate was observed]. MeOH (200 mL) was added and additional solvent was removed (ca. 200 mL) at 50° C. The heterogeneous mixture was cooled at −5° C. After 16 h, the solid was collected by vacuum filtration and washed with cold MeOH. The solid was dried under high vacuum to afford 32 g of 11 as an off-white solid. ¹H NMR (300 MHz, CDCl₃), mixture of rotamers: δ 11.22 (br s, 2H), 7.40 (dd, J=5.1, 8.7 Hz, 2H), 7.31 (d, J=9.3 Hz, 2H), 6.76 (dd, J=8.40, 8.40, 2H) 6.26 (br s, 2H), 5.44 (m, 2H), 4.39 (dd, J=7.5, 16.5 Hz, 2H), 4.24 (m, 2H), 4.15 (dd, J=5.1, 12.9 Hz, 2H), 3.79 (d, J=12.9 Hz, 2H), 3.10-3.30 (m, 4H), 2.32 (d, J=14.7 Hz, 2H), 2.24 (s, 6H), 1.90 (m, 2H), 1.74 (m, 2H), 1.56 (s, 18H), 0.99 (t, J=7.5 Hz, 6H) ppm; ¹³C NMR (75 MHz, CDCl₃): δ172.2, 170.4, 161.4, 158.3, 155.8, 137.0, 136.9, 128.6, 125.5, 118.9, 118.7, 108.6, 108.4, 108.1, 98.3, 98.0, 80.8, 74.7, 60.4, 53.8, 53.5, 34.1, 28.7, 28.6, 26.2, 21.5, 10.5 ppm. Mass spectrum (ESI), m/z 920.5 [(M)+; calcd for C₄₈H₆₂F₂N₆O₁₀: 921.0].

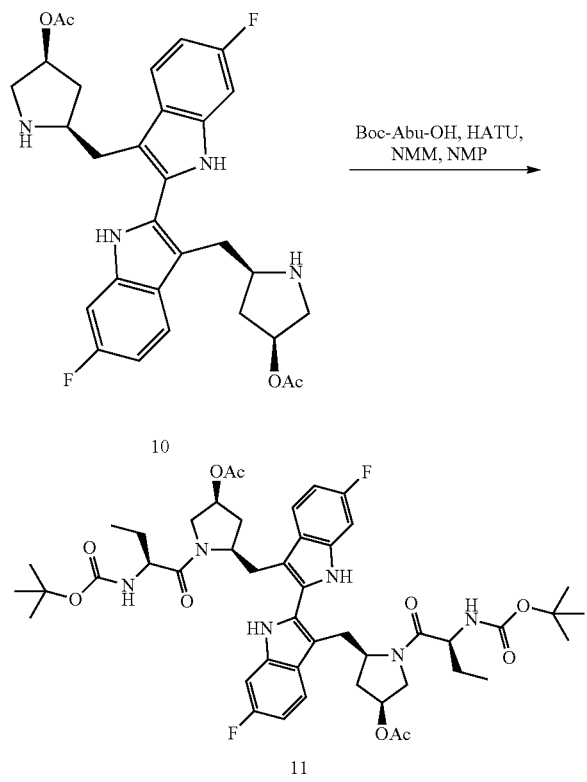

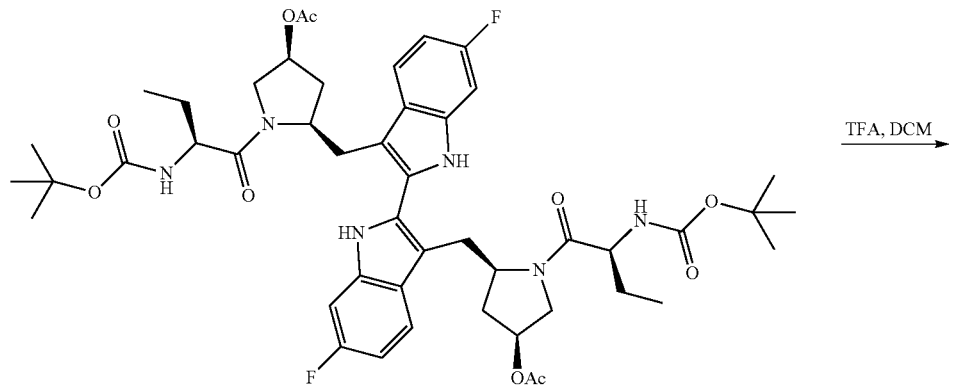

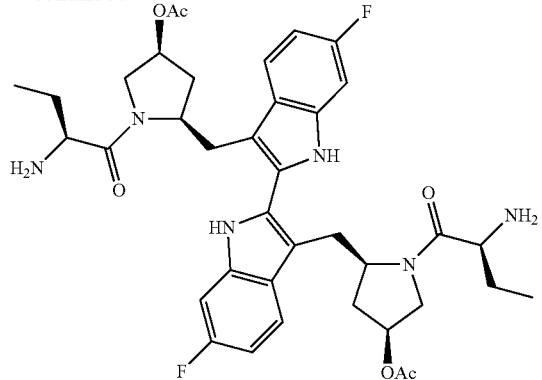

12

Acetic acid 5-{3'-[4-acetoxy-1-(2-amino-butyryl)-pyrrolidin-2-ylmethyl]-6,6'-difluoro-1H,1'H-[2,2']biindolyl-3-ylmethyl}-1-(2-amino-butyryl)-pyrrolidin-3-yl ester (12)

A solution containing 11 (27.5 g, 30 mmol) in DCM (200 mL) was cooled to 0° C. TFA (50 mL) was added and the reaction was monitored by LC/MS analysis until complete conversion of 11 to 12 (ca. 3 h). The solvent was removed in vacuo and the dark, green-colored residue was dissolved in EtOAc (ca. 1 L). The EtOAc solution was carefully poured into a saturated aqueous NaHCO₃/ice/water mixture to neutralize the residual TFA. The organic phase was separated and washed twice with saturated aqueous NaHCO₃ then once with brine. The combined aqueous washes were back-extracted with EtOAc (2×100 mL) and the combined organic extracts were dried over anhydrous Na₂SO₄, filtered, and concentrated to afford 22 g of crude 12 as an off-white solid. $^1$H NMR (300 MHz, CDCl$_3$+d$_4$-MeOH), mixture of rotomers: δ11.62 (br s, 2H), 7.48-7.62 (m, 4H), 6.89 (ddd, J=2.4, 9.3, 9.3 Hz, 2H), 5.48 (dd, J=4.5, 4.8 Hz, 2H), 4.52 (dd, J=9.3, 9.3 Hz, 2H), 4.06 (dd, J=4.8, 12.3 Hz, 2H), 3.78 (d, J=12.3 Hz, 2H), 3.54-3.70 (m, 4H), 3.30-3.40 (m, 2H), 2.33 (s, 6H), 2.02-2.16 (m, 2H), 1.70-1.96 (m, 4H), 1.09 (t, J=7.2 Hz, 6H) ppm; $^{13}$C NMR (75 MHz, CDCl$_3$+d$_4$-MeOH): δ173.5, 170.9, 161.8, 158.6, 137.2, 137.1, 128.2, 128.1, 125.6, 118.7, 118.6, 108.6, 108.3, 108.0, 98.6, 98.1, 74.6, 60.1, 53.5, 33.5, 28.0, 21.4, 9.7 ppm. Mass spectrum (ESI), m/z 721.4 [(M)+; calcd for C$_{38}$H$_{46}$F$_2$N$_6$O$_6$: 720.8].

Scheme XII

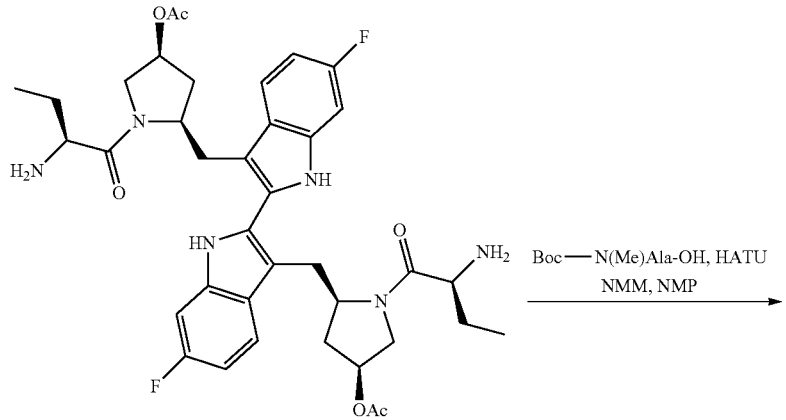

12

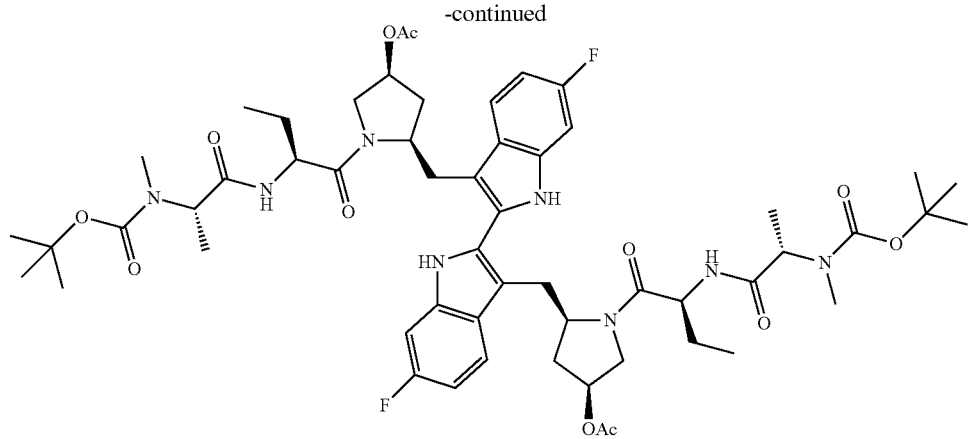

13

Acetic acid 5-(3'-{4-acetoxy-1-[2-(2-methyl-(tert-butoxycarbonyl)-amino-propionylamino)-butyryl]-pyrrolidin-2-ylmethyl}-6,6'-difluoro-1H,1'H-[2,2'] biindolyl-3-ylmethyl)-1-[2-(2-methyl-(tert-butoxycarbonyl)-amino-propionylamino)-butyryl]-pyrrolidin-3-yl ester (13)

To a solution containing Boc-N(Me)Ala-OH (14.6 g, 72 mmol) and HATU (30.4 g, 80 mmol) in anhydrous NMP (150 mL) at 0° C. was added NMM (12 mL, 105 mmol) followed by addition of 12 (30 mmol) in NMP (200 mL). The resulting mixture was allowed to warm to ambient temperature. After 16 h, the reaction mixture was diluted with diethyl ether (1 L) and washed successively with water (1 L), 1N HCl (2×100 mL), saturated aqueous NaHCO$_3$ (2×100 mL), brine, dried over anhydrous Na$_2$SO$_4$, filtered, concentrated to afford 33.5 g of crude 13.

The crude 13 was dissolved in EtOH (50 mL) and then slowly added to water (1000 mL) with vigorous stirring at 50° C. which resulted in the precipitation of a white solid. The heterogeneous mixture was cooled to −5° C. After 16 h, the solid was collected by vacuum filtration and washed with water. The wet solid was dried under high vacuum at 50° C. to afford 29.9 g of 13 as an off-white solid. $^1$H NMR (300 MHz, CDCl$_3$): δ11.57 (br s, 2H), 7.40-7.60 (m, 4H), 6.89 (m, 2H), 5.50 (m, 2H), 4.75 (m, 2H), 4.67 (q, J=6.9 Hz, 2H), 4.50 (t, J=9.6 Hz, 2H), 4.20 (dd, J=3.9, 12.3 Hz, 2H) 3.85 (d, J=12.3 Hz, 2H), 3.57 (br d, J=13.5 Hz, 2H), 3.34 (dd, J=12.0, 13.8 Hz, 2H), 2.89 (s, 6H), 2.34 (s, 6H), 2.10 (m, 2H), 1.95 (dt, J=6.0, 13.8 Hz, 2H), 1.79 (dt, J=7.2, 14.1 Hz, 2H), 1.52 (s, 18H), 1.39 (d, J=7.2 Hz, 6H), 1.03 (t, J=7.2 Hz, 6H) ppm; $^{13}$C NMR (75 MHz, CDCl$_3$): δ174.0, 172.1, 171.9, 170.5, 161.8, 158.7, 137.5, 137.3, 128.4, 125.8, 118.7, 118.6, 108.8, 108.4, 108.1, 98.8, 98.5, 81.0, 74.6, 60.1, 54.0, 52.0, 33.7, 30.5, 28.6, 28.1, 25.9, 21.6, 14.0, 9.9 ppm. Mass spectrum (ESI), m/z 1091.7 [(M)+; calcd for $C_{56}H_{76}F_2N_8O_{10}$: 1091.2].

Scheme XIII

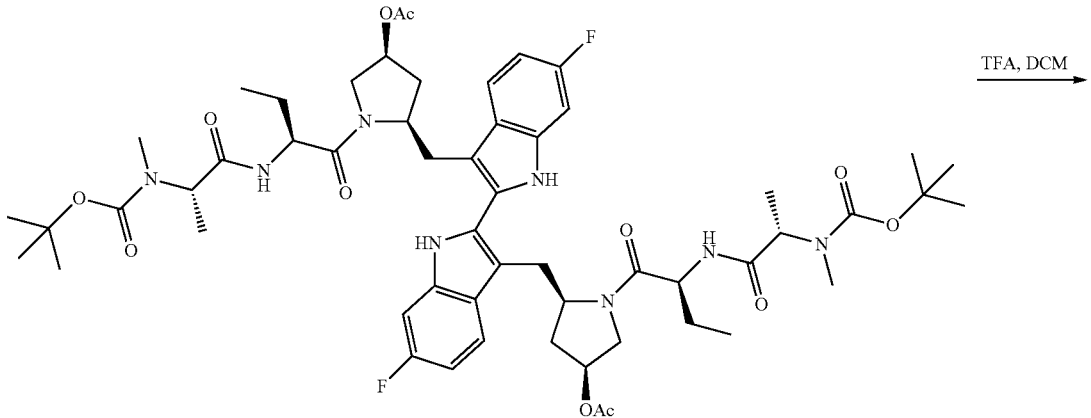

13

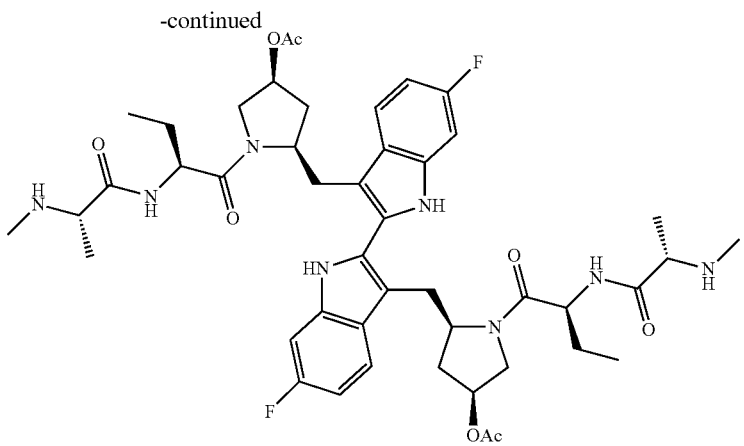

14

Acetic acid 5-(3'-{4-acetoxy-1-[2-(2-methylamino-propionylamino)-butyryl]-pyrrolidin-2-ylmethyl}-6,6'-difluoro-1H,1'H-[2,2']biindolyl-3-ylmethyl)-1-[2-(2-methylamino-propionylamino)-butyryl]-pyrrolidin-3-yl ester (14)

A solution containing 13 (28.5 g, 26 mmol) in DCM (150 mL) was cooled to 0° C. TFA (50 mL) was added. After 30 min, the reaction mixture was warmed to ambient temperature and monitored until LC/MS analysis revealed complete conversion of 13 to 14 (ca. 4 h). The solvent was removed in vacuo and the dark, green-colored residue was dissolved in EtOAc (500 mL) and carefully poured onto an aqueous NaHCO₃/ice mixture. The aqueous phase was separated and back-extracted with EtOAc (2×250 mL). The combined organic extracts were washed several times with saturated aqueous NaHCO₃, then brine, dried over anhydrous Na₂SO₄, filtered, and concentrated to afford 24 g of 14 as a light yellow-colored solid. $^1$H NMR (300 MHz, CDCl₃): δ11.66 (br s, 2H), 8.16 (d, J=8.4 Hz, 2H), 7.52 (dd, J=2.1, 9.6 Hz, 2H), 7.43 (dd, J=5.4, 8.4 Hz, 2H), 6.83 (ddd, J=2.1, 9.0, 9.0 Hz, 2H), 5.41 (dd, J=4.2, 4.5 Hz, 2H), 4.64 (dd, J=7.8, 14.1 Hz, 2H), 4.36 (br d, J=9.3, 9.6 Hz, 2H), 4.13 (dd, J=4.8, 12.6 Hz, 2H), 3.81 (d, J=12.0 Hz, 2H), 3.44 (d, J=13.2 Hz, 2H), 3.0-3.18 (m, 4H), 2.50 (s, 6H), 2.30 (s, 6H), 2.15 (d, J=14.4 Hz, 2H), 1.90-2.08 (m, 2H), 1.76-1.90 (m, 2H), 1.33 (d, J=7.2 Hz, 6H), 1.08 (t, J=7.2 Hz, 6H) ppm; $^{13}$C NMR (75 MHz, CDCl₃): δ175.3, 172.6, 170.4, 161.8, 137.5, 137.3, 128.4, 128.3, 125.9, 118.6, 118.5, 108.5, 108.1, 107.8, 98.7, 98.3, 74.5, 60.9, 59.9, 53.9, 51.3, 35.8, 33.6, 27.6, 26.2, 21.5, 20.2, 10.1 ppm. Mass spectrum (ESI), m/z 891.6 [(M)+; calcd for C₄₆H₆₀F₂N₈O₈: 891.0].

Scheme XIV

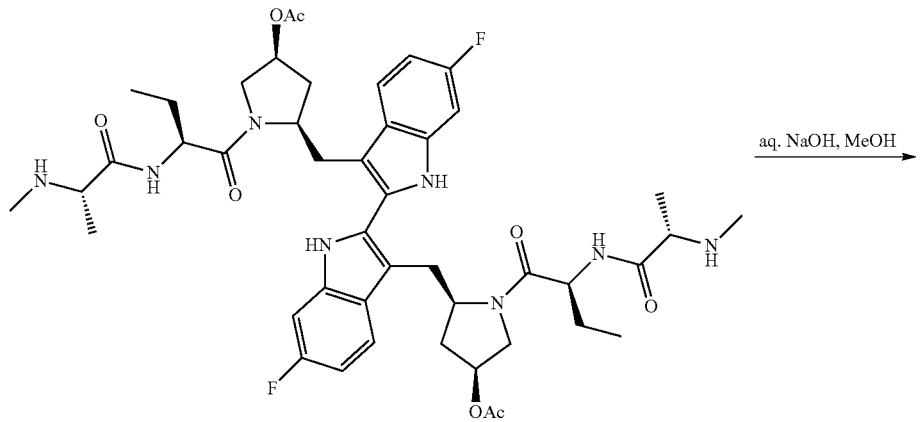

14

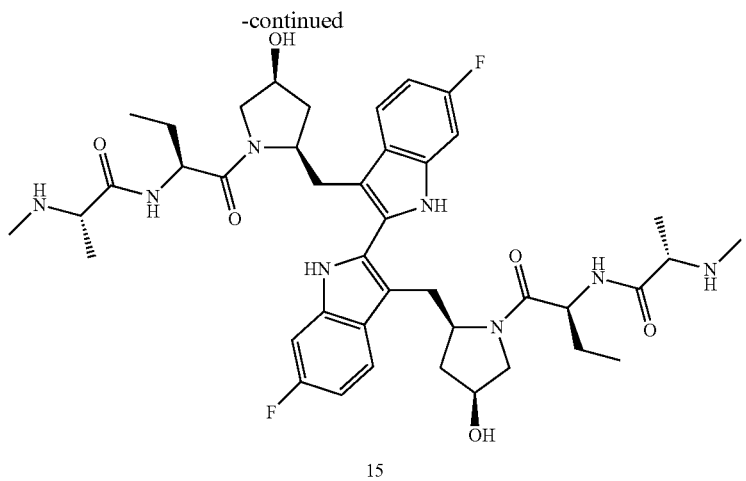

15

N-{1S-[2R-(6,6'-Difluoro-3'-{4S-hydroxy-1-[2S-(2S-methylamino-propionylamino)-butyryl]-pyrrolidin-2R-ylmethyl}-1H,1'H-[2,2']biindolyl-3-ylmethyl)-4S-hydroxy-pyrrolidine-1-carbonyl]-propyl}-2S-methylamino-propionamide (15)

To a solution containing 14 (24 g) in MeOH (200 mL) was added 1 M NaOH (80 mL) at 0° C. The reaction mixture was degassed and maintained under a nitrogen atmosphere wrapped with aluminum foil. The ice-bath was removed. After 60 min, the MeOH was removed in vacuo and the residue was diluted with water (200 mL) and extracted with EtOAc (500 mL). The aqueous phase was separated and back-extracted with EtOAc (2×150 mL). The combined organic extracts were washed with brine and dried over anhydrous $Na_2SO_4$, filtered, and concentrated to afford 22.5 g of crude 15 as a light, brown/yellow-colored solid.

The crude 15 (22.5 g) was dissolved in MeOH (50 mL) and EtOAc (200 mL). The volume was reduced (50%) by distillation at reduced pressure at 60° C. using a rotary evaporator. MTBE (300 mL) was added and the cloudy solution was warmed to 60° C. After 30 min, the solution was cooled to ambient temperature and then maintained at −5° C.

After 16 h, the solid was collected by vacuum filtration and washed with cold 25% EtOAc/MTBE and dried under high vacuum at ambient temperature to afford 16.6 g of 15 as an off-white solid. An additional 5.5 g of 15 was recovered from the filtrate via solvent removal and vacuum drying. $^1$H NMR (300 MHz, $CDCl_3$): δ11.74 (s, 2H), 8.27 (d, J=8.7 Hz, 2H), 7.71 (dd, J=5.4, 8.4 Hz, 2H), 7.55 (dd, J=2.4, 9.6 Hz, 2H), 6.88 (ddd, J=2.4, 9.3, 9.3 Hz, 2H), 4.62-4.78 (m, 4H), 4.43 (dd, J=9.3, 9.9 Hz, 2H), 4.03 (dd, J=4.8, 11.4 Hz, 2H), 3.80 (d, J=11.4 Hz, 2H), 3.66 (dd, J=2.7, 14.4 Hz, 2H), 3.53 (dd, J=11.4, 14.4 Hz, 2H), 3.11 (q, J=6.9 Hz, 2H), 2.56 (s, 6H), 2.45 (m, 2H), 2.19 (d, J=14.4 Hz, 2H), 1.76-2.10 (m, 6H), 1.59 (br s, 2H), 1.39 (d, J=6.9 Hz, 6H), 1.22-1.38 (m, 2H), 1.07 (t, J=7.2 Hz, 6H) ppm; $^{13}$C NMR (75 MHz, $d_6$-DMSO): δ175.2, 172.8, 161.6, 158.5, 137.3, 137.2, 128.4, 128.3, 126.4, 120.8, 120.6, 109.4, 108.7, 108.4, 98.4, 98.0, 70.8, 60.2, 59.9, 56.6, 51.8, 36.4, 35.3, 28.3, 25.6, 20.0, 10.6 ppm. Mass spectrum (ESI), m/z 807.5 [(M)+; calcd for $C_{42}H_{56}F_2N_8O_6$: 806.9].

Scheme XV

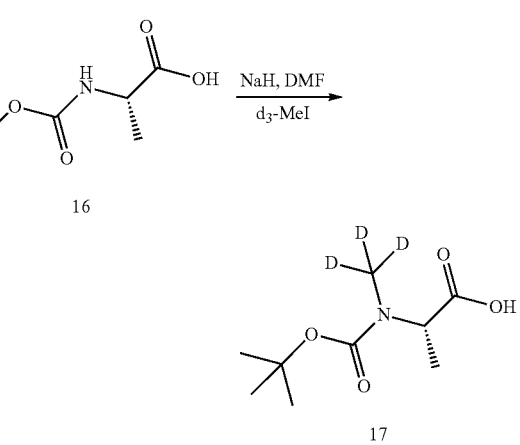

N-tert-butoxycarbonyl-N-($d_3$-methyl)alanine (17)

To a solution of Boc-Ala-OH (16, 3.5 g, 18.5 mmol) in anhydrous THF (50 mL) was added NaH (2.1 g, 60% in mineral oil, 51.0 mmol) at 0° C. After 45 min, the reaction mixture was warmed to ambient temperature and then warmed to 45° C. for an additional 20 min. The reaction mixture was cooled to 0° C. and $d_3$-iodomethane (10.0 g, 69.0 mmol) was added. The resulting mixture was stirred at ambient temperature. After 16 h, the reaction mixture was quenched with water, and extracted with EtOAc. The organic phase was discarded and the aqueous solution was acidified to pH 3 with 1N HCl and extracted with EtOAc. The organic phase was washed with brine, dried over anhydrous $Na_2SO_4$, filtered, and concentrated. The residue was purified by reverse-phase HPLC (Dynamax 2" C18 column; 10-100% ACN/water containing 0.1% HOAc over 30 min; 40 mL/min) to afford 17 (3.6 g, 94%) as a white solid following lyophilization. $^1$H NMR (300 MHz, $d_4$-MeOH), mixture of rotomers: δ4.80 (br s, 1H), 4.67 (q, J=6.9 Hz, 0.5H), 4.38 (q, J=6.9 Hz, 0.5H), 1.36-1.52 (m, 12H) ppm; Mass spectrum (ESI), m/z 207.0 [(M+H)+; calcd for $C_9H_{15}D_3NO_4$: 207.2].

Scheme XVI

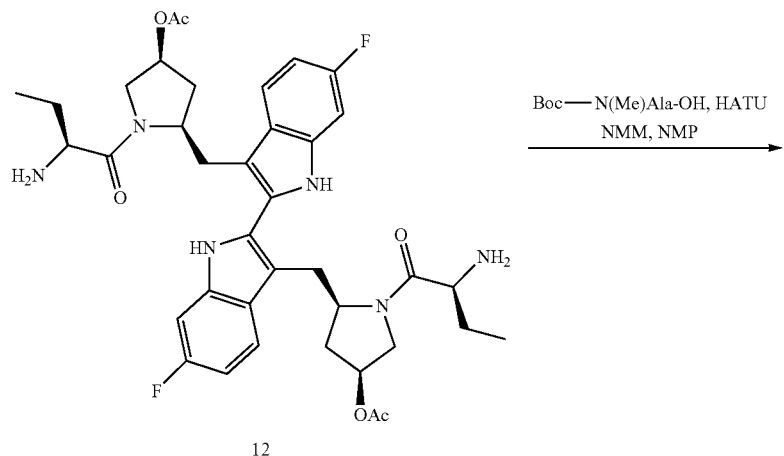

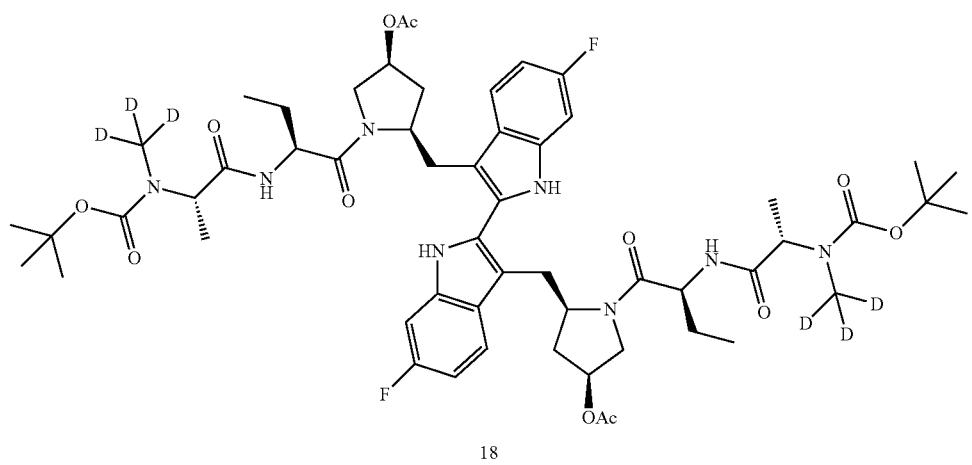

Acetic acid 5-(3'-{4-acetoxy-1-[2-(2-$d_3$-methyl-(tert-butoxycarbonyl)-amino-propionylamino)-butyryl]-pyrrolidin-2-ylmethyl}-6,6'-difluoro-1H,1'H-[2,2']biindolyl-3-ylmethyl)-1-[2-(2-$d_3$-methyl-(tert-butoxycarbonyl)-amino-propionylamino)-butyryl]-pyrrolidin-3-yl ester (18)

To a solution containing Boc-N($d_3$-Me)Ala-OH (17, 1.00 g, 4.83 mmol) and HATU (2.00 g, 5.30 mmol) in anhydrous NMP (20 mL) at 0° C. was added NMM (0.8 mL, 7.20 mmol) followed by addition of 12 (crude, 1.73 g, 2.40 mmol) in NMP (20 mL). The resulting mixture was allowed to warm to ambient temperature. After 16 h, the reaction mixture was diluted with diethyl ether (200 mL) and washed successively with water (200 mL), 1N HCl (2×100 mL), saturated aqueous NaHCO$_3$ (2×100 mL), brine, dried over anhydrous Na$_2$SO$_4$, filtered, concentrated. The residue was purified by reverse-phase HPLC (Dynamax 2" C18 column; 10-100% ACN/water containing 0.1% HOAc over 30 min; 40 mL/min). The product-containing fractions were combined, frozen, and lyophilized to afford 1.1 g of 18 (42%) as an off-white solid. $^1$H NMR (300 MHz, CDCl$_3$), mixture of rotomers: δ11.56 (br s, 2H), 7.56 (dd, J=5.4, 8.7 Hz, 2H), 7.52 (m, 2H), 7.10 (br s, 2H), 6.89 (ddd, J=2.1, 9.0, 9.0 Hz, 2H), 5.47 (t, J=4.8 Hz, 2H), 4.75 (br s, 2H), 4.67 (q, J=6.9 Hz, 2H), 4.50 (t, J=9.3 Hz, 2H), 4.18 (dd, J=4.2, 11.7 Hz, 2H) 3.85 (d, J=12.6 Hz, 2H), 3.57 (dd, J=2.1, 14.4 Hz, 2H), 3.34 (dd, J=12.0, 14.4 Hz, 2H), 2.34 (s, 6H), 2.29 (br s, 2H), 2.10 (m, 2H), 1.97 (m, 2H), 1.79 (m, 2H), 1.51 (s, 18H), 1.39 (d, J=6.9 Hz, 6H), 1.03 (t, J=7.5 Hz, 6H) ppm. Mass spectrum (ESI), m/z 1097.7 [(M)+; calcd for C$_{56}$H$_{70}$D$_6$F$_2$N$_8$O$_{12}$: 1097.3].

Scheme XVII

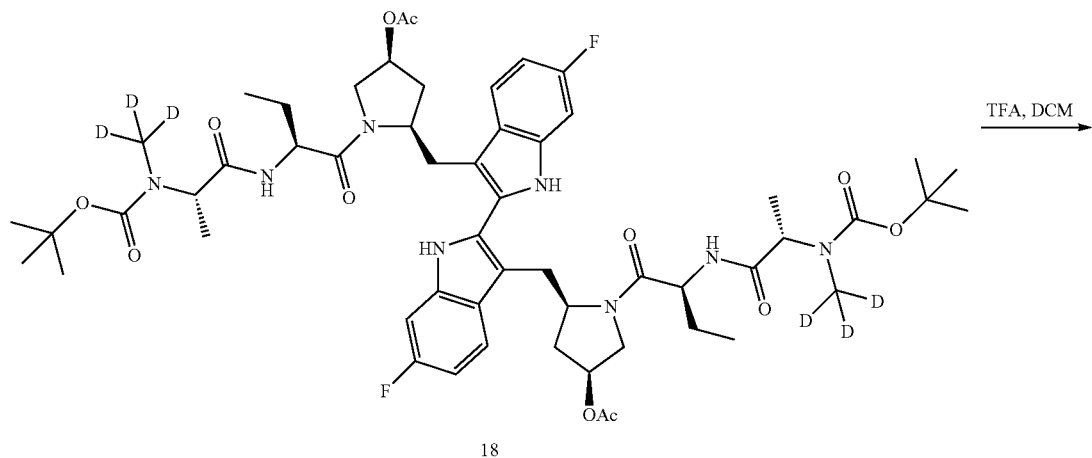

18

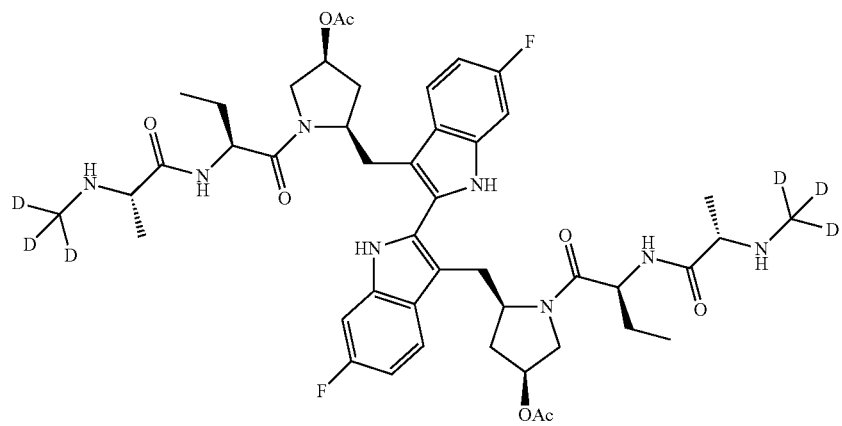

19

Acetic acid 5-(3'-{4-acetoxy-1-[2-(2-d-methyl-amino-propionylamino)-butyryl]-pyrrolidin-2-ylm-ethyl}-6,6'-difluoro-1H,1'H-[2,2']biindolyl-3-ylm-ethyl)-1-[2-(2-d$_3$-methylamino-propionylamino)-butyryl]-pyrrolidin-3-yl ester (19)

A solution containing 18 (1.10 g, 1.00 mmol) in DCM (15 mL) was cooled to 0° C. TFA (5 mL) was added. After 30 min, the reaction mixture was warmed to ambient temperature and monitored until LC/MS analysis revealed complete conversion of 18 to 19 (ca. 4 h). The solvent was removed in vacuo and the dark, green-colored residue was dissolved in EtOAc (100 mL) and carefully poured onto an aqueous NaHCO$_3$/ice mixture. The aqueous phase was separated and back-extracted with EtOAc (2×50 mL). The combined organic extracts were washed several times with saturated aqueous NaHCO$_3$, and then brine, dried over anhydrous Na$_2$SO$_4$, filtered, and concentrated to afford crude 19 which was used without further purification. Mass spectrum (ESI), m/z 897.5 [(M)+; calcd for C$_{46}$H$_{54}$D$_6$F$_2$N$_8$O$_8$: 897.0].

Scheme XVIII

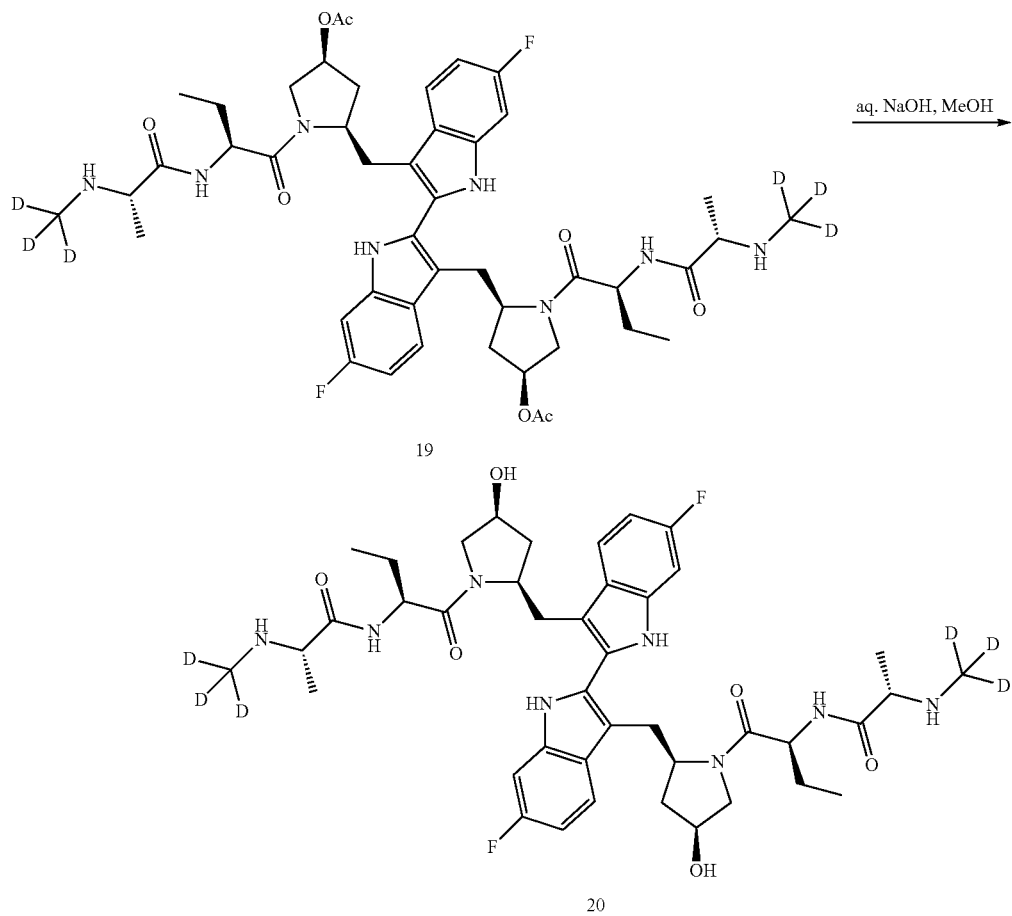

N-{1S-[2R-(6,6'-Difluoro-3'-{4S-hydroxy-1-[2S-(2S-d₃-methylamino-propionylamino)-butyryl]-pyrrolidin-2R-ylmethyl}-1H,1'H-[2,2']biindolyl-3-ylmethyl)-4S-hydroxy-pyrrolidine-1-carbonyl]-propyl}-2S-d₃-methylamino-propionamide (20)

To a solution containing crude 19 (ca. 1.00 mmol) in MeOH (20 mL) was added 1 M NaOH (2 mL) at ambient temperature. After 35 min, the MeOH was removed in vacuo and the residue was diluted with water (50 mL) and extracted with EtOAc (2×50 mL). The combined organic extracts were washed with brine and dried over anhydrous $Na_2SO_4$, filtered, and concentrated. The residue was purified by reverse-phase HPLC (Dynamax 2" C18 column; 10-100% ACN/water containing 0.1% HOAc over 30 min; 40 mL/min). The product-containing fractions were combined, frozen, and lyophilized to afford 0.6 g of 20 (75%) as a flocculent, white solid. $^1$H NMR (300 MHz, $CD_3CN$), mixture of rotamers: δ 11.86 (s, 2H), 7.91 (d, J=7.8 Hz, 2H), 7.71 (dd, J=5.4, 8.7 Hz, 2H), 7.45 (dd, J=2.4, 9.9 Hz, 2H), 6.83 (m, 2H), 4.56 (m, 2H), 4.47 (m, 2H), 4.20 (m, 2H), 3.84 (dd, J=4.2, 11.1 Hz, 2H), 3.66 (d, J=11.1 Hz, 2H), 3.45 (m, 4H), 2.93 (q, J=6.9 Hz, 2H), 1.60-1.89 (m, 8H), 1.19 (d, J=6.9 Hz, 6H), 0.94 (t, J=7.2 Hz, 6H) ppm; $^{13}$C NMR (75 MHz, $CD_3CN+d_4$-MeOH), mixture of rotamers: δ175.2, 173.0, 162.4, 159.3, 137.8, 137.6, 128.8, 128.7, 126.8, 110.8, 120.7, 109.5, 108.7, 108.4, 98.5, 98.1, 71.6, 60.5, 60.1, 56.8, 52.6, 36.6, 28.6, 26.0, 22.7, 19.0, 10.1 ppm. Mass spectrum (ESI), m/z 813.4 [(M)+; calcd for $C_{42}H_{50}D_6F_2N_8O_6$: 813.0].

Scheme XIX

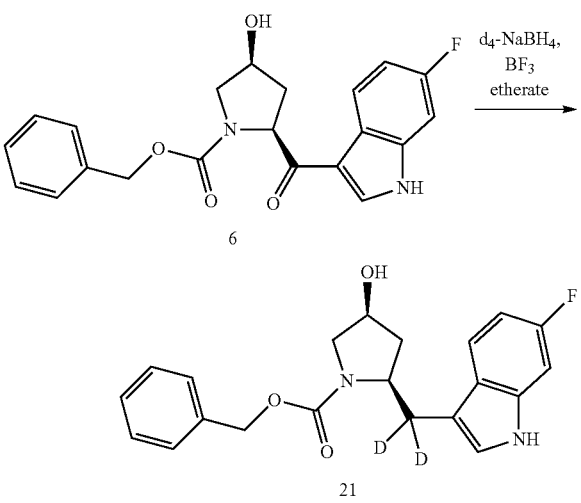

2-(6-Fluoro-1H-indol-3-yl-d$_2$-methyl)-4-hydroxy-pyrrolidine-1-carboxylic acid benzyl ester (21)

A suspension of 6 (3.0 g, 7.85 mmol) in anhydrous THF (50 mL) was cooled to 0° C. d$_4$-NaBH$_4$ (0.66 g, 15.7 mmol) was added in one portion followed by the addition of BF$_3$.etherate (1.1 mL, 8.60 mmol). After ca. 10 min, the ice bath was removed and the reaction mixture was warmed to reflux.

After 3 h, the reaction mixture was cooled in an ice-bath and carefully quenched with saturated aqueous NH$_4$Cl (50 mL). The biphasic mixture was diluted with EtOAc and the organic layer was separated and washed with water (2×50 mL) then brine. The EtOAc layer was dried over anhydrous Na$_2$SO$_4$, filtered, and concentrated to afford 3.2 g of crude 21 (>quant.) which was used without further purification. Mass spectrum (ESI), m/z 371.2 [(M+H)+; calcd for C$_{21}$H$_{20}$D$_2$FN$_2$O$_3$: 371.4].

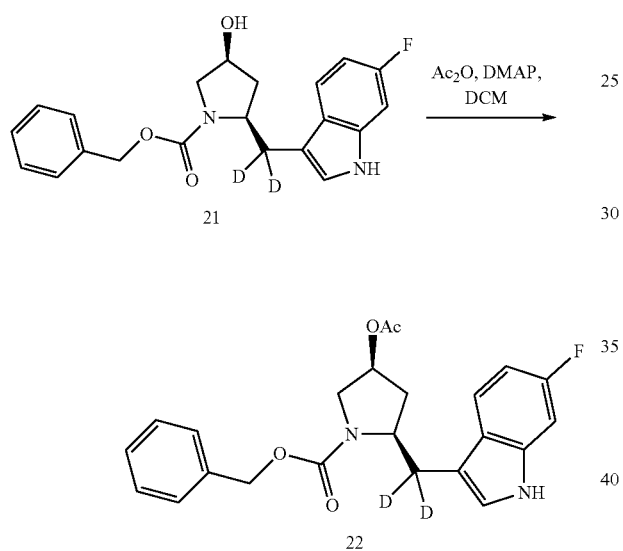

4-Acetoxy-2-(6-fluoro-1H-indol-3-yl-d$_2$-methyl)-pyrrolidine-1-carboxylic acid benzyl ester (22)

To a solution containing crude 21 (ca. 7.85 mmol), Et$_3$N (1.2 g, 12.0 mmol), and DMAP (50 mg, cat.) in DCM (30 mL) was added acetic anhydride (0.74 mL, 7.85 mmol) at ambient temperature. After 3 h, the reaction mixture was quenched with saturated aqueous NaHCO$_3$ (50 mL) then diluted with DCM. The DCM layer was separated and washed successively with dilute HCl (50 mL), water (50 mL), and brine (50 mL). The organic solution was dried over anhydrous Na$_2$SO$_4$, filtered, and concentrated. The crude product was purified by flash silica gel chromatography [30-40% EtOAc in hexane] to afford 2.0 g (62%, 2 steps) of 22 as a white foam. $^1$H NMR (300 MHz, CDCl$_3$), ~1:1 mixture of rotomers: δ8.41 (br s, 1H), 7.80-6.50 (m, 9H), 5.25 (m, 1H), 5.21 (m, 2H), 4.27 (m, 1H), 3.82 (dt, J=5.1, 13.2 Hz, 1H), 3.61 (dd, J=11.4, 11.7 Hz, 1H), 2.13 (s, 3H), 2.00 (m, 2H) ppm; $^{13}$C NMR (75 MHz, CDCl$_3$), ~1:1 mixture of rotomers: δ170.8, 160.2 (J$_{CF}$=236.2 Hz), 155.2, 136.9, 136.6, 136.5, 129.0, 128.9, 128.6 (J$_{CF}$=24.4 Hz), 124.5 (J$_{CF}$=22.1 Hz), 123.1, 120.1 (J$_{CF}$=27.2 Hz), 119.9 (J$_{CF}$=27.2 Hz), 112.8, 108.2 (J$_{CF}$=23.5 Hz), 97.7 (J$_{CF}$=25.7 Hz), 74.1, 73.3, 68.0, 67.2, 58.5, 57.6, 53.4, 53.1, 35.4, 34.6, 21.5 ppm. Mass spectrum (ESI), m/z 413.1 [(M)+; calcd for C$_{23}$H$_{21}$D$_2$FN$_2$O$_4$: 412.4].

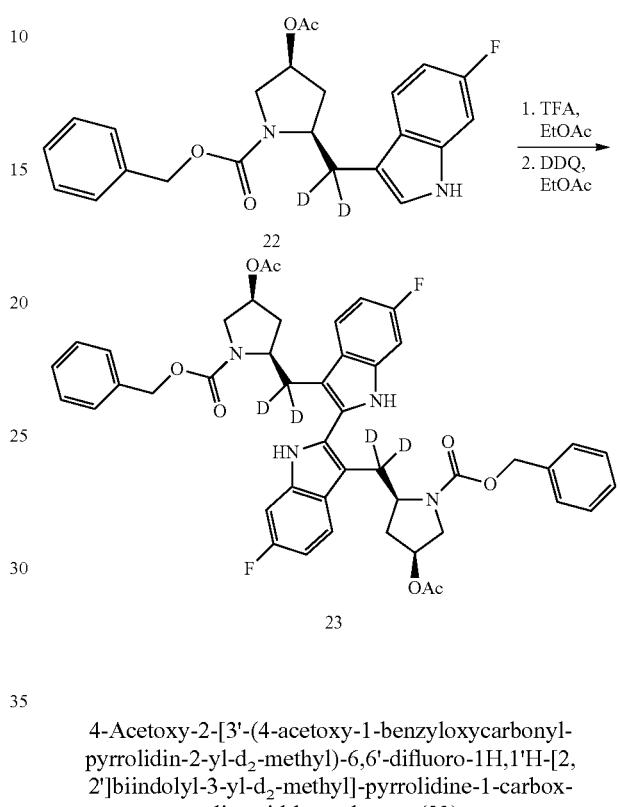

4-Acetoxy-2-[3'-(4-acetoxy-1-benzyloxycarbonyl-pyrrolidin-2-yl-d$_2$-methyl)-6,6'-difluoro-1H,1'H-[2,2']biindolyl-3-yl-d$_2$-methyl]-pyrrolidine-1-carboxylic acid benzyl ester (23)

Indole 22 (2.0 g, 4.80 mmol) was dissolved in pre-cooled (−5° C.) TFA (10 mL). The resulting yellow-colored solution was allowed to slowly warm to ambient temperature over 2 h. The reaction mixture was concentrated in vacuo to remove the TFA and the crude mixture of indolylindoline diastereomers was used directly in the next reaction. Mass spectrum (ESI), m/z 825.4 [(M)+; calcd for C$_{46}$H$_{42}$D$_4$F$_2$N$_4$O$_8$: 824.9].

To a solution containing the indolylindoline diastereomers in EtOAc (100 mL) was added DDQ (0.58 g, 2.5 mmol) in one portion. After 15 min, the dark orange/brown-colored reaction mixture was quenched with saturated aqueous NaHCO$_3$. The layers were separated and the organic phase was washed successively with saturated aqueous NaHCO$_3$ (3×50 mL) and brine, dried over anhydrous Na$_2$SO$_4$, filtered, and concentrated. The crude product was dissolved in DCM (10 mL) and the solution was then diluted with MeOH (50 mL). Slow removal of the DCM in vacuo afforded a precipitate which was collected by vacuum filtration, washed with cold MeOH, and dried to provide 1.7 g of 23 (86%, 2 steps). $^1$H NMR (300 MHz, CDCl$_3$): δ11.30 (br s, 2H), 7.60-7.30 (m, 14H), 6.90 (app. dt, J=2.4, 9.3 Hz, 2H), 5.40 (m, 2H), 5.36 (d, J=3.6 Hz, 4H), 4.28 (d, J=8.1 Hz, 2H), 3.79 (m, 4H), 2.31 (s, 6H), 2.06 (m, 4H) ppm; Mass spectrum (ESI), m/z 823.3 [(M)+; calcd for C$_{46}$H$_{40}$D$_4$F$_2$N$_4$O$_8$: 822.9].

Scheme XXII

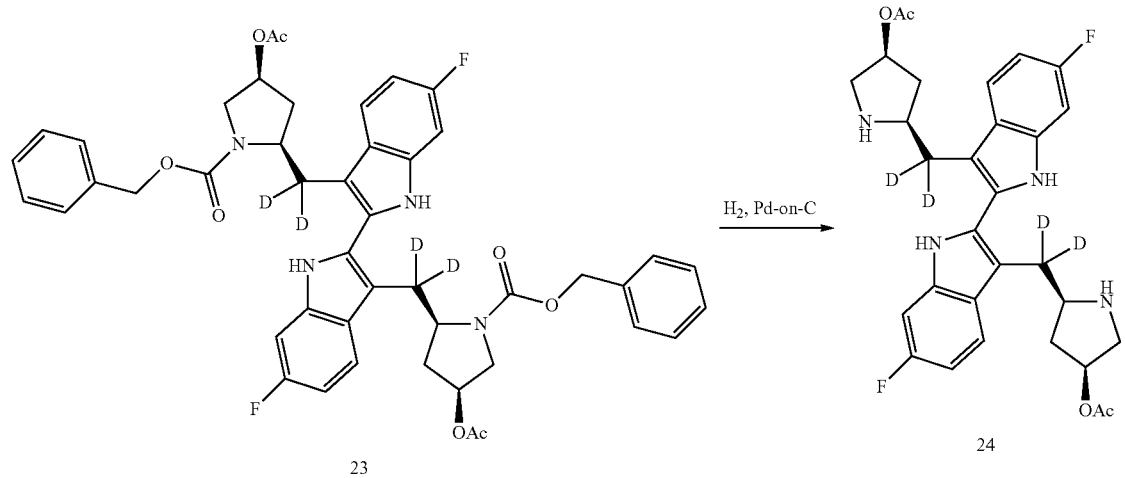

Acetic acid 5-[3'-(4-acetoxy-pyrrolidin-2-yl-d₂-methyl)-6,6'-difluoro-1H,1'H-[2,2']biindolyl-3-yl-d₂-methyl]-pyrrolidin-3-yl ester (24)

A suspension containing 23 (0.40 g, 0.48 mmol) in 1:1 EtOAc/MeOH (40 mL) was placed in a 500 mL Parr bottle and charged with 10% Pd-on-C (wet, ca. 200 mg). The reaction mixture was pressurized to 50 PSI H₂ and shaken for 3 h. The reaction mixture was filtered through a pad of Celite® and the solids were washed with EtOAc. The clarified filtrate was concentrated in vacuo to afford crude 24 as an off-white solid which was used directly in the next reaction. Mass spectrum (ESI), m/z 555.2 [(M)+; calcd for C₃₀H₂₈D₄F₂N₄O₄: 554.6].

Scheme XXIII

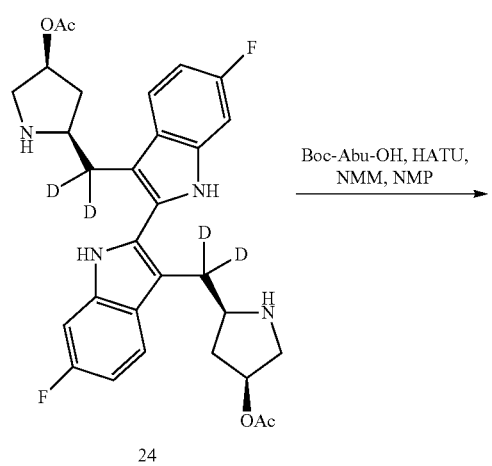

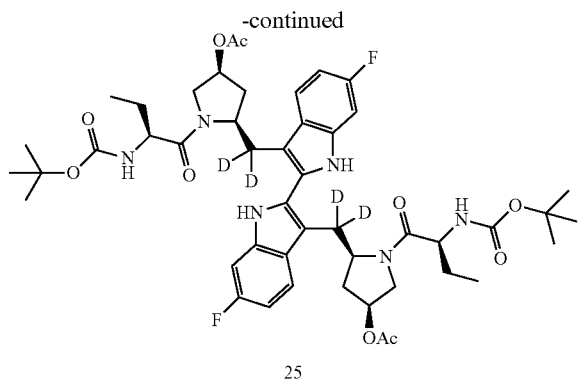

Acetic acid 5-{3'-[4-acetoxy-1-(2-tert-butoxycarbonylamino-butyryl)-pyrrolidin-2-yl-d₂-methyl]-6,6'-difluoro-1H,1'H-[2,2']biindolyl-3-yl-d₂-methyl}-1-(2-tert-butoxycarbonylamino-butyryl)-pyrrolidin-3-yl ester (25)

To a solution containing Boc-Abu-OH (224 mg, 1.1 mmol) and HATU (442 mg, 1.2 mmol) in anhydrous NMP (10 mL) at 0° C. was added NMM (0.2 mL, 1.7 mmol) followed by a solution of 24 (0.48 mmol) in NMP (10 mL). The reaction mixture was slowly warmed to ambient temperature. After 16 h, the reaction mixture was diluted with diethyl ether (100 mL) and the mixture was washed successively with water (5×50 mL), 1N HCl (50 mL), saturated aqueous NaHCO₃ (50 mL), and brine, dried over anhydrous Na₂SO₄, filtered, and concentrated. The crude product was purified by reverse-phase HPLC (Dynamax 2" C18 column; 10-100% ACN/water containing 0.1% HOAc over 30 min; 40 mL/min). The product-containing fractions were combined, concentrated, and lyophilized to afford 310 mg of 25 (70%, 2 steps) as a flocculent white solid. ¹H NMR (300 MHz, CDCl₃), mixture of rotamers: δ11.17 (br s, 2H), 7.39 (dd, J=5.4, 8.4 Hz, 2H), 7.29 (d, J=9.3 Hz, 2H), 6.75 (dd, J=8.40, 8.40, 2H), 6.40 (br s, 2H), 5.44 (m, 2H), 4.40 (dd, J=7.8, 16.5 Hz, 2H), 4.22 (d, J=7.8 Hz, 2H), 4.15 (dd, J=5.1, 12.9 Hz, 2H), 3.80 (d, J=12.9 Hz, 2H), 2.23 (s, 6H), 1.90 (m, 2H), 1.74 (m, 2H), 1.57 (s, 18H), 0.99 (t, J=7.2 Hz, 6H) ppm; $^{13}$C NMR (75 MHz, CDCl$_3$), mixture of rotomers: δ172.1, 170.4, 161.4, 158.2, 155.8, 137.0, 136.9, 128.6, 125.5, 118.9, 118.8, 108.6, 108.4, 108.1, 98.3, 98.0, 80.8, 74.7, 60.3, 53.8, 53.6, 34.1, 28.7, 28.6 (br), 26.2, 21.5, 10.5 ppm. Mass spectrum (ESI), m/z 925.4 [(M)+; calcd for C$_{48}$H$_{58}$D$_4$F$_2$N$_6$O$_{10}$: 925.0].

Acetic acid 5-{3'-[4-acetoxy-1-(2-amino-butyryl)-pyrrolidin-2-yl-d$_2$-methyl]-6,6'-difluoro-1H,1'H-[2,2']biindolyl-3-yl-d$_2$-methyl}-1-(2-amino-butyryl)-pyrrolidin-3-yl ester (26)

A solution containing 25 (310 mg, 0.34 mmol) in DCM (20 mL) was cooled to 0° C. TFA (5 mL) was added and the reaction was monitored by LC/MS analysis until complete conversion of 25 to 26 (ca. 3 h). The solvent was removed in vacuo and the dark, green-colored residue was dissolved in EtOAc (50 mL). The EtOAc solution was carefully poured into a saturated aqueous NaHCO$_3$/ice/water mixture Scheme XXIV

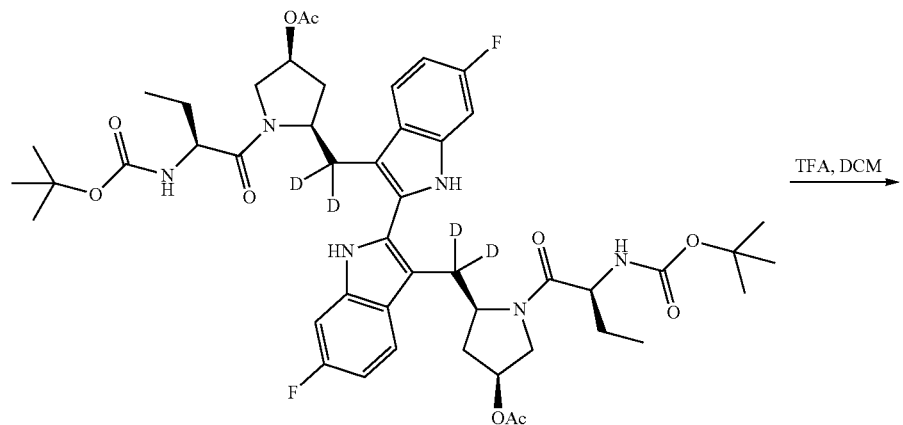

25

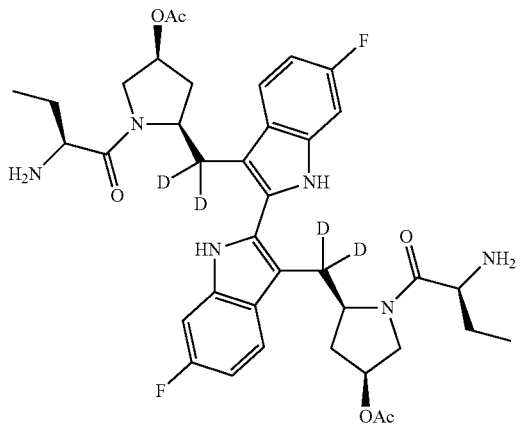

26 to neutralize the residual TFA. The organic phase was separated and washed twice with saturated aqueous NaHCO$_3$ then once with brine. The combined aqueous washes were back-extracted with EtOAc (2×20 mL) and the combined organic extracts were dried over anhydrous Na$_2$SO$_4$, filtered, and concentrated to afford crude 26 (250 mg) as an off-white solid. Mass spectrum (ESI), m/z 725.3 [(M)+; calcd for C$_{38}$H$_{42}$D$_4$F$_2$N$_6$O$_6$: 724.8].

with water (50 mL), 1N HCl (2×50 mL), saturated aqueous NaHCO$_3$ (2×50 mL), brine, dried over anhydrous Na$_2$SO$_4$, filtered, concentrated. The crude product was purified by reverse-phase HPLC (Dynamax 2" C18 column; 10-100% ACN/water containing 0.1% HOAc over 30 min; 40 mL/min). The product-containing fractions were combined, concentrated, and lyophilized to afford 170 mg of 27 (91%, 2 steps) as a flocculent, off-white solid. $^1$H NMR (300 MHz, Scheme XXV

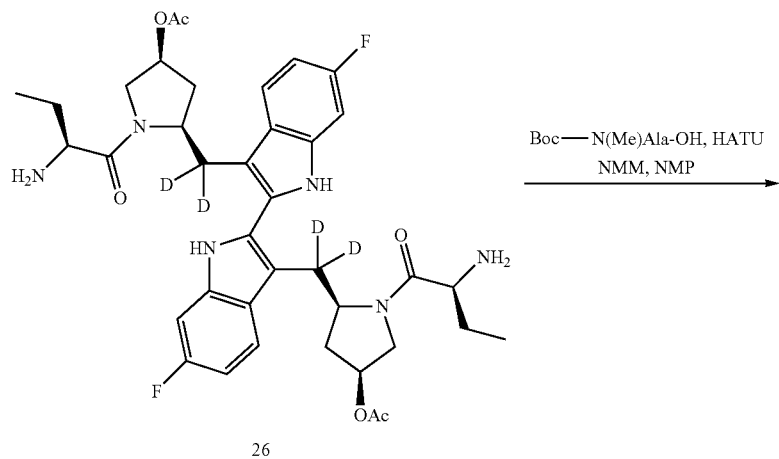

26

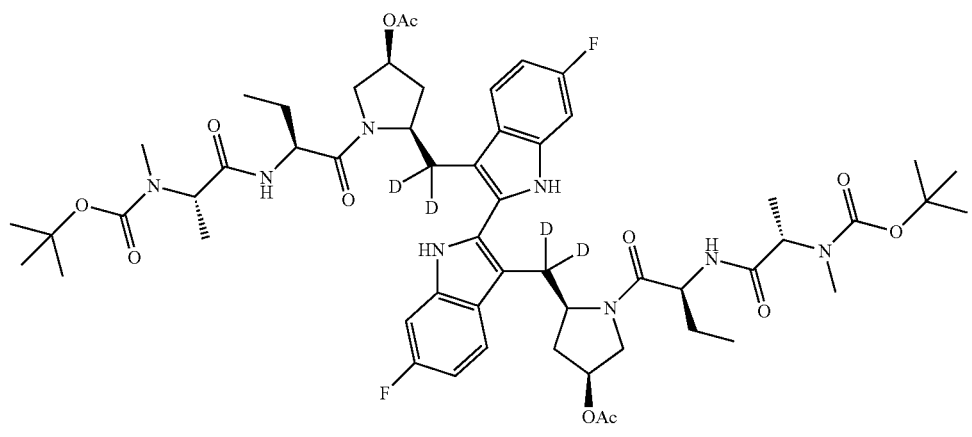

27

Acetic acid 5-(3'-{4-acetoxy-1-[2-(2-methyl-(tert-butoxycarbonyl)-amino-propionylamino)-butyryl]-pyrrolidin-2-yl-d$_2$-methyl}-6,6'-difluoro-1H,1'H-[2,2']biindolyl-3-yl-d$_2$-methyl)-1-[2-(2-methyl-(tert-butoxycarbonyl)-amino-propionylamino)-butyryl]-pyrrolidin-3-yl ester (27)

To a solution containing Boc-N(Me)Ala-OH (83 mg, 0.41 mmol) and HATU (172 mg, 0.45 mmol) in anhydrous NMP (5 mL) at 0° C. was added NMM (0.1 mL, 0.85 mmol) followed by addition of crude 26 (123 mg, 0.17 mmol) in NMP (5 mL). The resulting mixture was allowed to warm to ambient temperature. After 16 h, the reaction mixture was diluted with diethyl ether (100 mL) and washed successively CDCl$_3$), mixture of rotamers: δ11.51 (br s, 2H), 7.40-7.60 (m, 4H), 6.86 (m, 2H), 5.46 (m, 2H), 4.74 (br s, 2H), 4.65 (q, J=6.9 Hz, 2H), 4.45 (d, J=8.7 Hz, 2H), 4.17 (dd, J=4.8, 12.3 Hz, 2H) 3.82 (d, J=12.3 Hz, 2H), 2.87 (s, 6H), 2.28 (s, 6H), 2.05 (m, 2H), 1.92 (m, 2H), 1.78 (m, 2H), 1.48 (s, 18H), 1.37 (d, J=7.2 Hz, 6H), 1.01 (t, J=7.2 Hz, 6H) ppm; $^{13}$C NMR (75 MHz, CDCl$_3$), mixture of rotamers: δ173.3, 170.2, 170.1, 170.5, 168.6, 159.9, 135.5, 135.4, 126.5, 126.4, 123.8, 116.8, 116.7, 106.8, 106.4, 106.1, 96.8, 96.5, 79.1, 72.6, 57.9, 52.1, 50.1, 31.7, 28.5, 26.6, 25.5 (br), 23.9, 19.6, 19.0, 12.1, 8.0 ppm. Mass spectrum (ESI), m/z 1095.5 [(M)+; calcd for C$_{56}$H$_{72}$D$_4$F$_2$N$_8$O$_{12}$: 1095.3].

Scheme XXVI

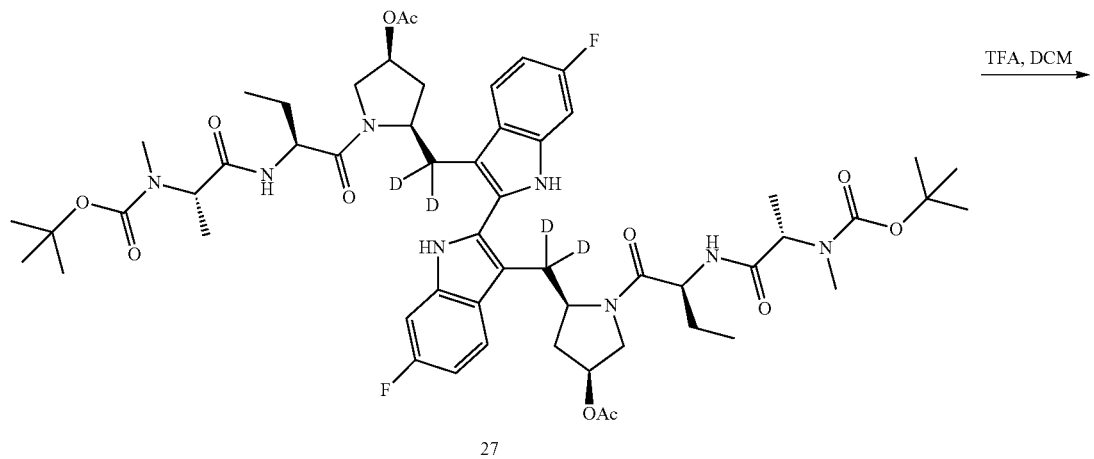

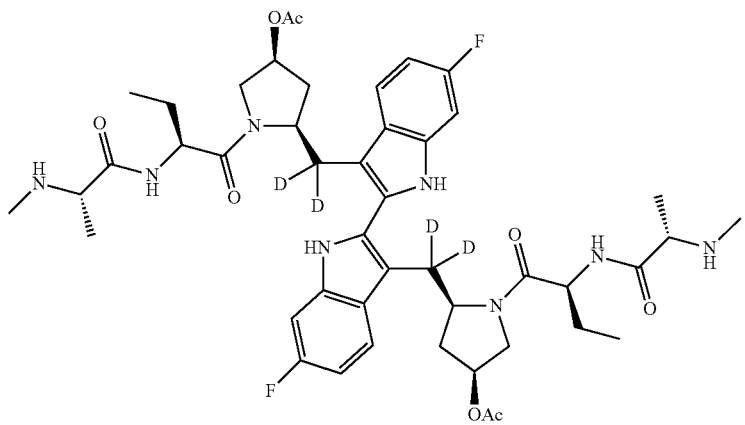

Acetic acid 5-(3'-{4-acetoxy-1-[2-(2-methylamino-propionylamino)-butyryl]-pyrrolidin-2-yl-d$_2$-methyl}-6,6'-difluoro-1H,1'H-[2,2']biindolyl-3-yl-d$_2$-methyl)-1-[2-(2-methylamino-propionylamino)-butyryl]-pyrrolidin-3-yl ester (28)

A solution containing 27 (170 mg, 0.15 mmol) in DCM (15 mL) was cooled to 0° C. TFA (5 mL) was added. After 30 min, the reaction mixture was warmed to ambient temperature and monitored until LC/MS analysis revealed complete conversion of 27 to 28 (ca. 4 h). The solvent was removed in vacuo and the dark, green-colored residue was dissolved in EtOAc (100 mL) and carefully poured onto an aqueous NaHCO$_3$/ice mixture. The aqueous phase was separated and back-extracted with EtOAc (2×20 mL). The combined organic extracts were washed several times with saturated aqueous NaHCO$_3$, then brine, dried over anhydrous Na$_2$SO$_4$, filtered, and concentrated to afford crude 28 as a light yellow-colored solid. Mass spectrum (ESI), m/z 895.3 [(M)+; calcd for C$_{46}$H$_{56}$D$_4$F$_2$N$_8$O$_8$: 895.0].

Scheme XXVII

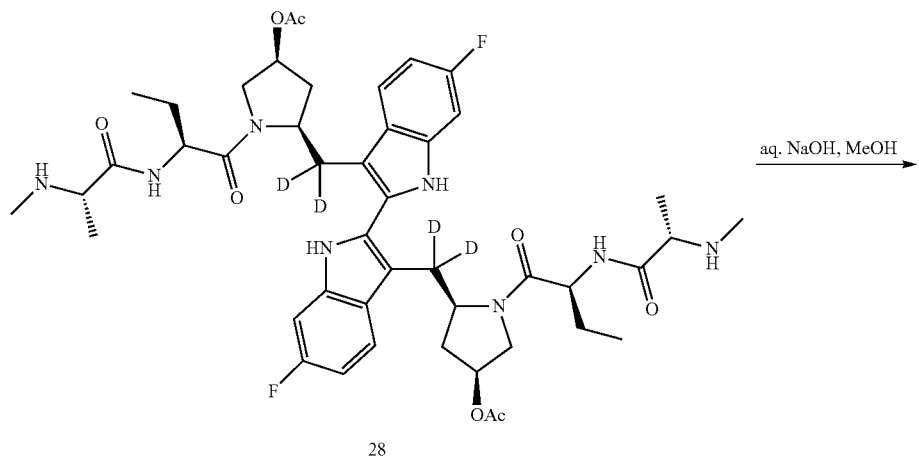

28

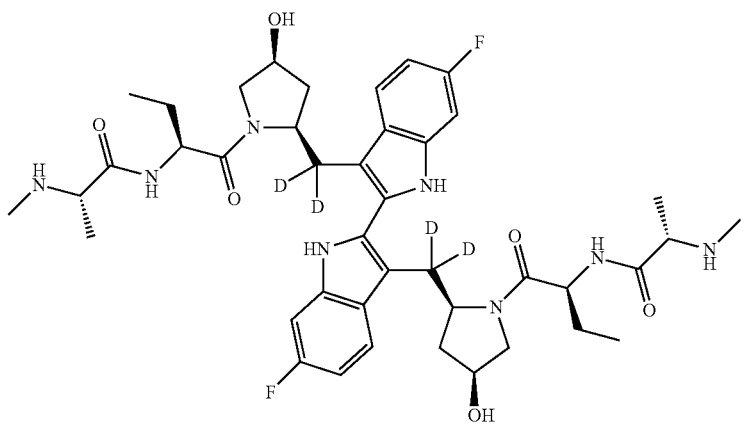

29

N-{1S-[2R-(6,6'-Difluoro-3'-{4S-hydroxy-1-[2S-(2S-methylamino-propionylamino)-butyryl]-pyrrolidin-2R-yl-$d_2$-methyl}-1H,1'H-[2,2']biindolyl-3-yl-$d_2$-methyl)-4S-hydroxy-pyrrolidine-1-carbonyl]-propyl}-2S-methylamino-propionamide (29)

To a solution containing crude 28 (0.15 mmol) in MeOH (20 mL) was added 1 M NaOH (5 mL) at 0° C. The reaction mixture was degassed and maintained under a nitrogen atmosphere wrapped with aluminum foil. The ice-bath was removed. After 60 min, the MeOH was removed in vacuo and the residue was diluted with water (20 mL) and extracted with EtOAc (50 mL). The aqueous phase was separated and back-extracted with EtOAc (2×50 mL). The combined organic extracts were washed with brine and dried over anhydrous $Na_2SO_4$, filtered, and concentrated. The crude product was purified by reverse-phase HPLC (Dynamax 2" C18 column; 10-100% ACN/water containing 0.1% HOAc over 30 min; 40 mL/min). The product-containing fractions were combined, concentrated, and lyophilized to afford 110 mg of 29 (90%, 2 steps) as a flocculent, white-colored solid. $^1$H NMR (300 MHz, $CDCl_3$+$d_4$-MeOH), mixture of rotomers: δ11.58 (s, 2H), 7.80 (dd, J=5.4, 8.7 Hz, 2H), 7.45 (dd, J=2.4, 9.9 Hz, 2H), 6.87 (ddd, J=2.4, 9.2, 9.2 Hz, 2H), 4.66 (dd, J=5.7, 7.8 Hz, 2H), 4.60 (br s, 2H), 4.47 (d, J=7.2 Hz, 2H), 4.00 (dd, J=4.8, 11.4 Hz, 2H), 3.76 (d, J=11.4 Hz, 2H), 3.43 (q, J=6.9 Hz, 2H), 2.55 (s, 6H), 2.19 (d, J=14.4 Hz, 2H), 1.78-2.02 (m, 8H), 1.46 (d, J=7.2 Hz, 6H), 1.09 (t, J=7.2 Hz, 6H) ppm; $^{13}$C NMR (75 MHz, $CDCl_3$+$d_4$-MeOH), mixture of rotomers: δ173.6, 171.8, 161.7, 158.6, 137.1, 136.9, 128.1, 128.0, 125.9, 119.8, 119.7, 108.3, 108.2, 107.8, 97.8, 97.5, 70.9, 69.4, 59.0, 56.1, 52.0, 36.3, 35.7, 25.5, 18.5, 9.8 ppm. Mass spectrum (ESI), m/z 811.4 [(M)+; calcd for $C_{42}H_{52}D_4F_2N_8O_6$: 810.9].

Scheme XXVIII

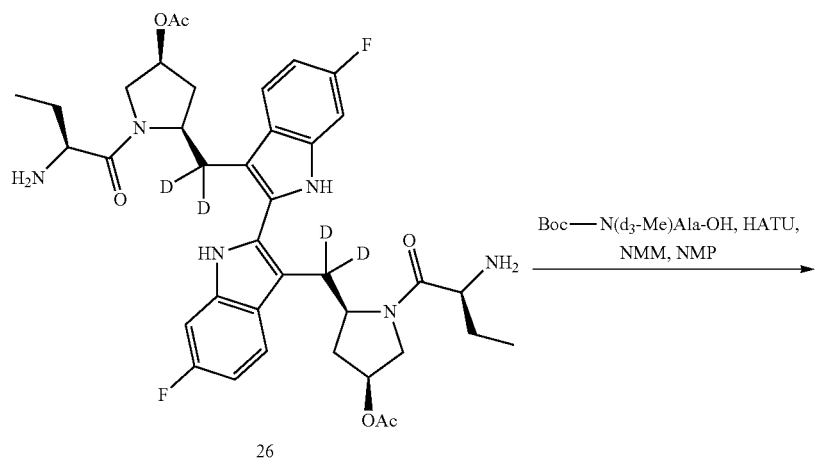

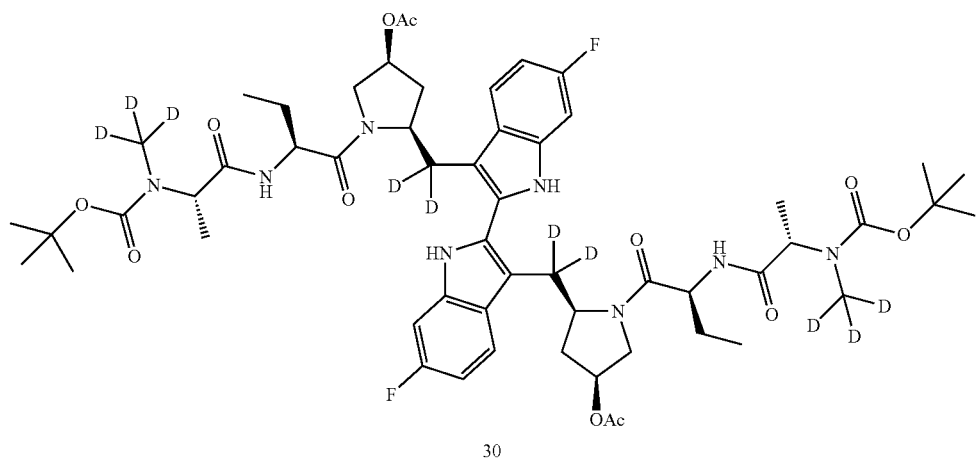

Acetic acid 5-(3'-{4-acetoxy-1-[2-(2-d₃-methyl-(tert-butoxycarbonyl)-amino-propionylamino)-butyryl]-pyrrolidin-2-yl-d₂-methyl}-6,6'-difluoro-1H,1'H-[2,2']biindolyl-3-yl-d₂-methyl)-1-[2-(2-d₃-methyl-(tert-butoxycarbonyl)-amino-propionylamino)-butyryl]-pyrrolidin-3-yl ester (30)

To a solution containing Boc-N(d₃-Me)Ala-OH (17, 83 mg, 0.41 mmol) and HATU (172 mg, 0.45 mmol) in anhydrous NMP (5 mL) at 0° C. was added NMM (0.1 mL, 0.85 mmol) followed by addition of crude 26 (123 mg, 0.17 mmol) in NMP (5 mL). The resulting mixture was allowed to warm to ambient temperature. After 16 h, the reaction mixture was diluted with diethyl ether (100 mL) and washed successively with water (50 mL), 1N HCl (2×50 mL), saturated aqueous NaHCO₃ (2×50 mL), brine, dried over anhydrous Na₂SO₄, filtered, concentrated. The crude product was purified by reverse-phase HPLC (Dynamax 2" C18 column; 10-100% ACN/water containing 0.1% HOAc over 30 min; 40 mL/min). The product-containing fractions were combined, concentrated, and lyophilized to afford 160 mg of 30 (85%, 2 steps) as a flocculent, white-colored solid. $^1$H NMR (300 MHz, CDCl₃), mixture of rotomers: δ11.51 (br s, 2H), 7.40-7.60 (m, 4H), 6.87 (ddd, J=2.1, 9.0, 9.0 Hz, 2H), 5.47 (t, J=4.8 Hz, 2H), 4.74 (br s, 2H), 4.65 (q, J=7.2 Hz, 2H), 4.46 (d, J=8.1 Hz, 2H), 4.18 (dd, J=3.9, 11.7 Hz, 2H) 3.83 (d, J=12.3 Hz, 2H), 2.30 (s, 6H), 2.24 (m, 2H), 2.05 (m, 2H), 1.93 (m, 2H), 1.79 (m, 2H), 1.49 (s, 18H), 1.38 (d, J=6.9 Hz, 6H), 1.02 (t, J=7.2 Hz, 6H) ppm; $^{13}$C NMR (75 MHz, CDCl₃), mixture of rotomers: δ175.6, 172.2, 172.1, 170.6, 161.8, 158.7, 137.5, 137.3, 128.5, 128.4, 125.8, 118.7, 118.6, 108.7, 108.4, 108.0, 98.8, 98.4, 81.1, 74.6, 66.1, 59.9, 54.0, 52.1, 33.7, 28.6, 27.5 (br), 25.8, 21.6, 20.9, 14.0, 9.9 ppm; Mass spectrum (ESI), m/z 1101.5 [(M)+; calcd for $C_{56}H_{66}D_{10}F_2N_8O_{12}$: 1101.3].

Scheme XXIX

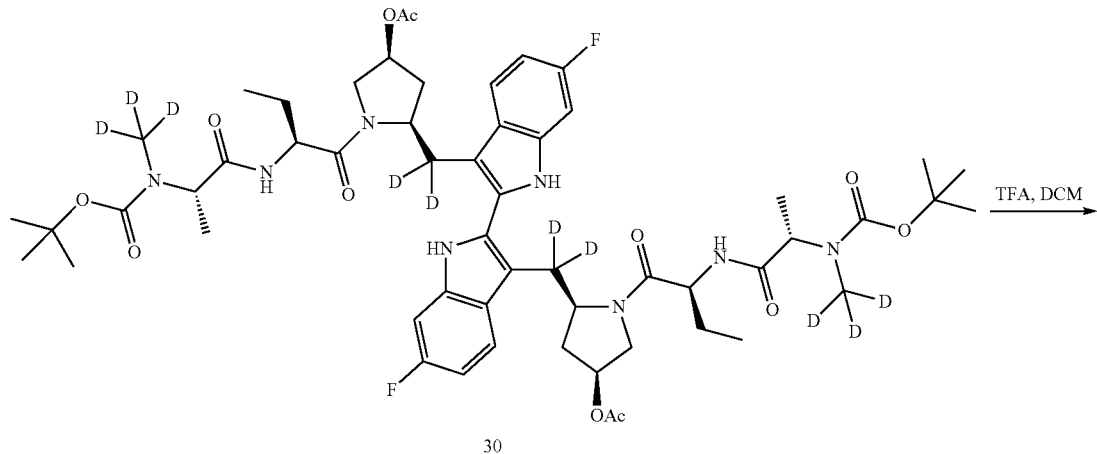

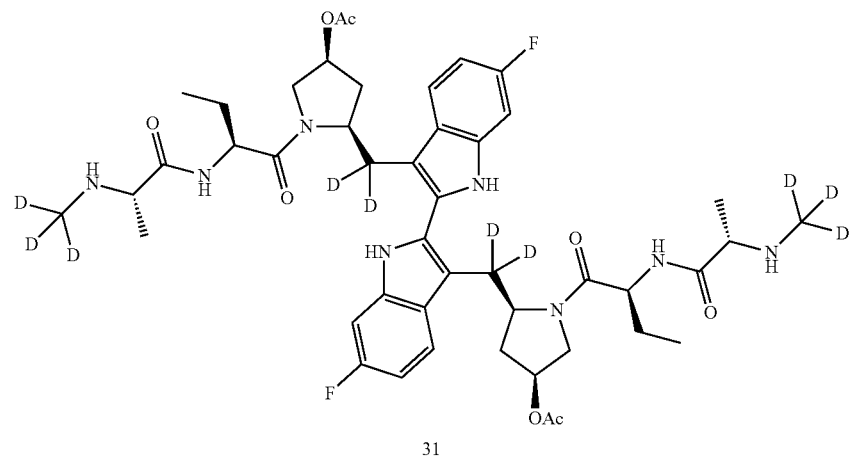

Acetic acid 5-(3'-{4-acetoxy-1-[2-(2-d$_3$-methyl-amino-propionylamino)-butyryl]-pyrrolidin-2-yl-d$_2$-methyl}-6,6'-difluoro-1H,1'H-[2,2']biindolyl-3-yl-d$_2$-methyl)-1-[2-(2-d$_3$-methylamino-propionylamino)-butyryl]-pyrrolidin-3-yl ester (31)

A solution containing 30 (160 mg, 0.14 mmol) in DCM (15 mL) was cooled to 0° C. TFA (5 mL) was added. After 30 min, the reaction mixture was warmed to ambient temperature and monitored until LC/MS analysis revealed complete conversion of 30 to 31 (ca. 4 h). The solvent was removed in vacuo and the dark, green-colored residue was dissolved in EtOAc (100 mL) and carefully poured onto an aqueous NaHCO$_3$/ice mixture. The aqueous phase was separated and back-extracted with EtOAc (2×20 mL). The combined organic extracts were washed several times with saturated aqueous NaHCO$_3$, then brine, dried over anhydrous Na$_2$SO$_4$, filtered, and concentrated to afford crude 31 as a light yellow-colored solid. Mass spectrum (ESI), m/z 901.5 [(M)+; calcd for C$_{46}$H$_{50}$D$_{10}$F$_2$N$_8$O$_8$: 901.1].

Scheme XXX

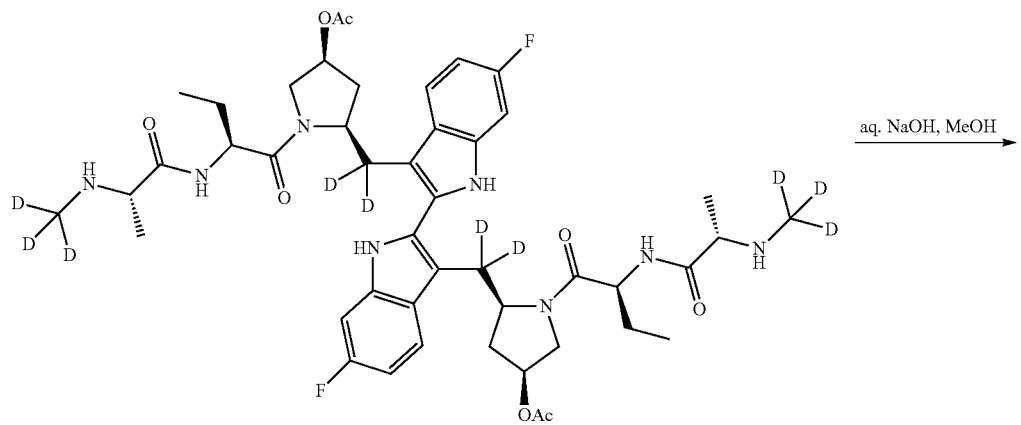

31

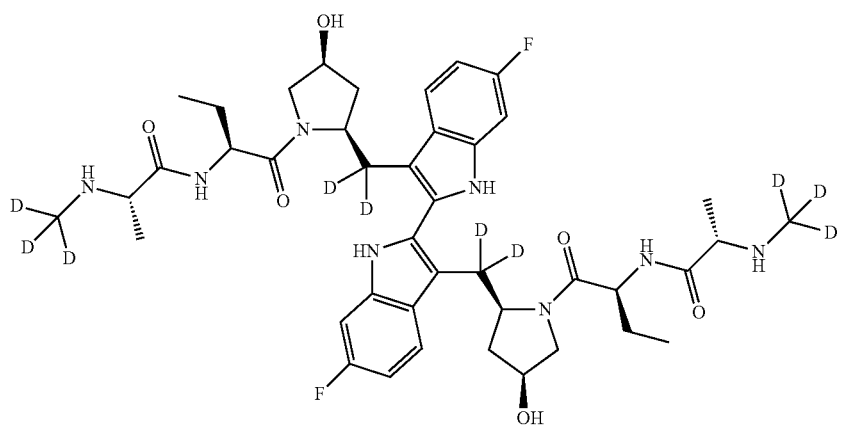

32

N-{1S-[2R-(6,6'-Difluoro-3'-{4S-hydroxy-1-[2S-(2S-methylamino-propionylamino)-butyryl]-pyrrolidin-2R-yl-$d_2$-methyl}-1H,1'H-[2,2']biindolyl-3-yl-$d_2$-methyl)-4S-hydroxy-pyrrolidine-1-carbonyl]-propyl}-2S-methylamino-propionamide (32)

To a solution containing crude 31 (0.14 mmol) in MeOH (20 mL) was added 1 M NaOH (5 mL) at 0° C. The reaction mixture was degassed and maintained under a nitrogen atmosphere wrapped with aluminum foil. The ice-bath was removed. After 60 min, the MeOH was removed in vacuo and the residue was diluted with water (20 mL) and extracted with EtOAc (50 mL). The aqueous phase was separated and back-extracted with EtOAc (2×50 mL). The combined organic extracts were washed with brine and dried over anhydrous $Na_2SO_4$, filtered, and concentrated. The crude product was purified by reverse-phase HPLC (Dynamax 2" C18 column; 10-100% ACN/water containing 0.1% HOAc over 30 min; 40 mL/min). The product-containing fractions were combined, concentrated, and lyophilized to afford 100 mg of 32 (87%, 2 steps) as a flocculent, white-colored solid. $^1$H NMR (300 MHz, $CDCl_3+d_4$-MeOH), mixture of rotomers: δ 11.62 (s, 2H), 7.79 (dd, J=5.4, 8.4 Hz, 2H), 7.47 (dd, J=2.4, 10.2 Hz, 2H), 6.87 (ddd, J=2.4, 9.2, 9.2 Hz, 2H), 4.68 (dd, J=5.4, 7.5 Hz, 2H), 4.58 (m, 2H), 4.45 (d, J=6.6 Hz, 2H), 3.99 (dd, J=4.8, 11.1 Hz, 2H), 3.75 (d, J=11.1 Hz, 2H), 3.19 (q, J=6.9 Hz, 2H), 2.15 (br d, J=12 Hz, 2H), 1.78-2.02 (m, 8H), 1.39 (d, J=6.6 Hz, 6H), 1.07 (t, J=7.5 Hz, 6H) ppm; $^{13}$C NMR (75 MHz, $CDCl_3+d_4$-MeOH), mixture of rotomers: δ175.4, 172.0, 161.8, 158.7, 137.1, 137.0, 128.2, 128.0, 126.0, 119.9, 119.7, 108.4, 108.3, 107.9, 98.0, 97.6, 71.0, 60.0, 59.6, 56.2, 51.6, 36.4, 25.8, 19.5, 9.8 ppm; Mass spectrum (ESI), m/z 817.4 [(M)+; calcd for $C_{42}H_{46}D_{10}F_2N_8O_6$: 817.0].

Examples 2, 3, 4, and 5

Compounds tested in Examples 2, 3, 4, and 5 are shown in Table 1.

TABLE 1

| Compound | R5 | R |
|---|---|---|
| 15 | —CH2CH3 | 6-F |
| 2 | —CH(CH3)CH3 | 6-F |
| 3 | —R—CH(OH)CH3 | 6-F |
| 4 | —S—CH(OH)CH3 | 6-F |
| 5 | —R—CH(OCH3)CH3 | 6-F |

Example 2A. cIAP Degradation Assay

The concentration inducing degradation of cIAP-1 and cIAP-2 by 50% ($IC_{50}$) for various compounds was determined by monitoring the disappearance of Green Fluorescent Protein (GFP)-signal in A375 cells. Briefly, A375 cell lines expressing GFP-tagged cIAP-1 and cIAP-2 were generated by transfecting HA2×EGFP-pcDNA3 vector containing either cIAP-1 (A375Gc1) or cIAP-2 (A375Gc2) coding region. $2\times10^4$ of A375Gc1 or A375Gc2 cells were grown in 96-well plate and treated with various concentrations of test compounds for 2 h. After incubation, cells were collected by trypsinization and suspended in 150 µl of DMEM-10% FBS. A total of $10^4$ cells were analyzed using a FACScan (Becton Dickinson). GFP fluorescence was monitored by using an excitation filter at 488 nm and emission was measured with a 530 nm filter. $IC_{50}$ is defined as the concentration of drug at which 50% of GFP signal was inhibited. Results of the cIAP-1 and -2 degradation assay are shown in Table 2.

TABLE 2

| Compound | GFP-cIAP-1 $IC_{50}$ (nM) | SD | GFP-cIAP-2 $IC_{50}$ (nM) | SD | IC50 Ratio cIAP-2/cIAP-1 |
|---|---|---|---|---|---|
| 15 | 27 (n = 56) | 15 | 174 (n = 61) | 100 | 6.4 |
| 2 | 4 (n = 3) | 0.6 | 7 (n = 3) | 0.8 | 1.8 |
| 3 | 328 (n = 3) | 83 | 674 (n = 3) | 69 | 2.1 |
| 4 | 464 (n = 12) | 112 | 604 (n = 12) | 192 | 1.3 |
| 5 | 10 (n = 41) | 2 | 37 (n = 38) | 19 | 3.7 |

These data show that Compound 15 has greater relative potency in degrading cIAP-1 relative to cIAP-2 when compared to Compounds 2, 3, 4, and 5.

Example 2B. Caspase-3 Derepression Assay

Exponentially growing MDA-MB-231 tumor cells (ATCC) were harvested by trypsinization and collected by centrifugation in a table top centrifuge at 1000×g for 10 minutes at room temperature. Cell pellet was washed one time by resuspending in 5 mL hypotonic lysis buffer (20 mM HEPES, pH7.5, 10 mM KCl, 1.5 mM $MgCl_2$, 1.0 mM EDTA, 1.0 mM DTT) and recollected by centrifugation. Pellet was next resuspended in 1 volume of hypotonic lysis buffer supplemented with a complete protease inhibitor tablet (Roche) and allowed to swell on ice for 30 minutes. Cells were disrupted by approximately 50 passages through a 27 gauge needle. Lysis was monitored by light microscopy. Lysate was centrifuged at 12000×g for 10 minutes at 4° C. to remove membrane fraction, unlysed cells and debris. The soluble fraction was collected for protein concentration determination and subsequent assay analysis.

The hypotonic lysate (25 µg protein), 50 µg/mL cytochrome c and 10 mM dATP were combined in a microcentrifuge tube to a final volume of 9 µl in hypotonic lysis buffer followed by addition of test compound and incubated for 30 minutes at room temp. Following incubation 50 µl of hypotonic lysis buffer containing 5 µM of pro-fluorescent rhodamine-110$_{(2)}$ based caspase-3 substrate zDEVD-R110$_{(2)}$ was added and fluorescence intensity was monitored over time. Activation of the lysate by addition of cytochrome c and dATP results in apoptosome formation and subsequent activation of caspases-9 and -3. Endogenous XIAP inhibits much of this activity and addition of test compound to the activated lysate results in more caspase activity than is generated by activated lysate alone as measured by increase in fluorescence intensity upon cleavage of zDEVD-R110$_{(2)}$ by caspase-3. $IC_{50}$ values were calculated using GraphPad Prism by plotting increase in fluorescence intensity vs. different concentrations of compounds tested and the results are shown in Table 3.

TABLE 3

| Compound | XIAP Caspase-3 Derepression $IC_{50}$ (nm) | SD |
|---|---|---|
| 15 | 24.3 (n = 3) | 2.0 |
| 2 | 13.4 (n = 3) | 4.3 |
| 3 | 0.2 (n = 3) | 0 |
| 4 | 0.35 (n = 3) | 0.2 |
| 5 | 0.36 (n = 3) | 0.05 |

These data show that Compound 15 has a lower potency for antagonizing XIAP function in comparison to Compounds 2, 3, 4, and 5.

Example 3—Cytotoxicity

SKOV-3 ovarian tumor cell cytotoxicity data were generated substantially as follows. The MTT (3-(4,5-Dimethylthiazol-2-yl)-2,5-diphenyltetrazolium bromide) assay is an example of an assay that has been used for measuring cell growth as previously described (Hansen, M. B., Nielsen, S. E., and Berg, K. (1989) *J. Immunol. Methods* 119, 203-210) and incorporated herein by reference in its entirety. Briefly, SK-OV-3 cells were seeded in 96-well plates in McCoy's medium containing 10% fetal bovine serum albumin (5,000 per well) and incubated overnight at 37° C. The next day, test compounds were added at various concentrations (0.003-10 µM) and the plates were incubated at 37° C. for an additional 72 hrs. This incubation time was optimal for measuring inhibitory effects of different analogs. Fifty microliters of 5 mg/mL MTT reagent to each well was added and the plates were incubated at 37° C. for 3 hours. At the end of the incubation period, 50 microliters of DMSO was added to each well to dissolve cells and the optical density (OD) of the wells was measured using a microplate reader (Victor² 1420, Wallac, Finland) at 535 nm. Cell survival (CS) was calculated by the following equation:

CS=(OD treated well/mean OD control wells)×100%

The $CC_{50}$, defined as the drug concentration that results in 50% CS, was derived by calculating the point where the dose-response curve crosses the 50% CS point using GraphPad Prism. These results suggest that Smac mimetics that bind to cIAP-1 can be used in the treatment of cancer either as monotherapy or in combination with chemotherapeutics. The results of SKOV-3 cytotoxicity assays for the compounds tested in this assay are shown in Table 4.

TABLE 4

| Compound | $CC_{50}$ (nM) | Std Dev (nM) |
| --- | --- | --- |
| 15 | 0.14 (n = 76) | 0.02 |
| 2 | 0.5 (n = 6) | 0.1 |
| 3 | 13 (n = 4) | 4 |
| 4 | 2 (n = 23) | 0.3 |
| 5 | 0.13 (n = 76) | 0.1 |

These data indicate that Compound 15 has equivalent potency to Compound 5 and is more potent than Compounds 2, 3, and 4.

Example 4—Toxicity

Body weight loss (BWL), mortality and additional toxicity data were generated substantially as follows. Sprague-Dawley rats were dosed daily (QDx4, i.v. bolus slow push) with Compounds 15, 4 and 5. Body weights were taken on day 4 and are shown as percent change from day 1. Compounds 4 and 5 were administered at 0.3 mg/Kg, 1 mg/Kg, or 3 mg/Kg; Compound 15 was administered at 1, 5, or 10 mg/Kg.

The results of the BWL assay are shown in FIG. 1.

Mortality.

Compounds 4 and 5 were not tolerated at 3 mg/Kg, and caused the animals to die at this dose. No mortality was observed with Compound 15 at 5 mg/Kg (mortality was observed at 10 mg/Kg.)

Clinical Results.

There were no clinical signs noted at 1 mg/kg/day with Compound 15 after 4 days of administration. Animals treated with Compound 15 at 5 mg/kg/day exhibited clinical signs similar to Compounds 4 and 5 at 1 mg/kg/day such as lethargy, increased/irregular respiration and increased heart rate. Rats treated with 1 mg/kg Compound 5 exhibited additional clinical observations including dehydration, ungroomed appearance, chromorhinorrhea, alopecia (head), and excessive scratching from days 2 to 4.

Body Weight.

At 1 mg/Kg, animals receiving Compounds 4 and 5 lost weight whereas animals receiving Compound 15 at 1 mg/kg/day gained weight. At 5 mg/kg/day with Compound 15, a treatment related mean body weight loss of approximately 8% was noted from day 1 to day 4. A treatment-related mean body weight loss of approximately 4% and 6% was noted in animals treated with Compounds 4 and 5, respectively, at 1 mg/kg/day.

Pathology.

Assessment of anatomic pathology after treatment with Compounds 4 and 5 at 1 mg/kg/day resulted in the following findings. There was marked to severe bone marrow hypocellularity of the erythroid series, mild to moderate hypercellularity of the myeloid series, and mild to moderate hypertrophy and hyperplasia of megakaryocytes in the tibia and sternum when Compounds 4 and 5 were administered at 1 mg/kg/day. For Compounds 4 and 5 the lungs had dose-related mild to moderate diffuse hypertrophy/hyperplasia of Type 2 pneumocytes which were accompanied by an increase in alveolar macrophages, hypertrophied bronchiolar epithelium, proliferating perivascular mononuclear cells and hypertrophied visceral pleural cells. In contrast, assessment of anatomic pathology following treatment with Compound 15 at the same dose (1 mg/kg/day) identified minimal to mild hypocellularity of erythroid cells, minimal to mild hypercellularity of myeloid cells, and minimal Type 2 pneumocyte hypertrophy in the lungs.

The data described above indicate that Compound 15 is approximately 5-fold better tolerated in the rat as compared to Compounds 4 and 5 on a dose per dose basis.

Example 5—Tumor Volume Reduction and Body Weight Change

MDA-MB-231 xenograft data were generated substantially as follows. MDA-MB-231 human breast tumor cells were injected into the mammary fat pad of female nude mice and dosing initiated twelve days later at an average tumor volume of approximately 148 mm³. No tumor burden was associated with this model based on lack of weight loss or animal morbidity in control groups. Mice were injected subcutaneously into the mammary fat pad with $1\times10^7$ cells suspended in 200 µl of a 1:1 HBSS: Matrigel solution; injected cells were within nine passages of the original lot. Pre-study tumor volumes were recorded beginning approximately one week prior to the estimated start date. When tumors reached approximately 150 mm³ animals are matched by tumor volume into treatment and control groups and dosing initiated (Day 0); mice are tagged and followed individually throughout the experiment. Animals were dosed by weight (0.01 mL per gram; 10 ml/Kg).

Beginning on Day 0, animals were observed daily and weighed twice weekly using a digital scale (Ohaus SP601); data including individual and mean gram weights (Mean We±SD), mean percent weight change versus Day 0 (% $vD_0$) and mean percent weight change versus prior measurement (% $vD_{-x}$) were recorded for each group and plotted at study completion. Beginning on Day 0, tumor dimensions were measured twice weekly by digital caliper (Fowler Ultra-Cal IV) and data including individual and mean estimated tumor volumes (Mean TV±SEM) recorded for each group; tumor volume was calculated using the formula: TV=width²×length×0.52. Individual mice reaching the designated study endpoint (an estimated tumor volume of approximately 1 cm³) were assigned a time to endpoint (TTE) value corresponding to that day; the tumor growth delay (TGD) study was concluded once all mice reach the study endpoint or sixty days following study initiation. At study completion, TGD and % TGD are calculated using the median TTE (MTTE) value for each treatment (T) group versus control (C) by the formulas: $TGD_{(days)}$=T−C and % TGD=T−C/C×100, wherein T−C is the difference between MTTE-Treatment Group and MTTE-Control. Tumored animals not reaching the designated volume endpoint by study completion are considered long-term survivors (LTS) and assigned a TTE value corresponding to the final study day; tumor-free animals are not included in TGD calculations. A Log-rank test is used to determine statistically significant differences in overall survival experience between each treated group compared to control. Individual mice reporting a tumor volume ≤50% of the Day 0 measurement for two consecutive measurements over a seven day period were considered partial responders (PR). If the PR persisted until study completion, percent tumor regression (% TR) was determined using the formula: % TR=1−T$_f$/T$_i$×100; a mean value was calculated if multiple PR mice occurred in one group. Individual mice lacking palpable tumors (<4×4 mm$^2$ for two consecutive measurements over a seven day period) were classified as complete responders (CR); a CR that persisted until study completion was considered a tumor-free survivor (TFS); TFS animals are excluded from TGD calculations and statistical analysis. Statistical differences in MTTE values between control and treatment groups are compared using a Log Rank test.

Compound 15 was administered by i.p. injection alone at 20, 40 or 60 mg/Kg on a q3dx5 schedule (every three days for 5 cycles). T–C values of 22 days were calculated for these groups, all of which were found statistically significant compared with control (p=0.005, p<0.0001, or p=0.0001). In the 20 mg/Kg group, 6/10 mice were considered long-term survivors and partial tumor regression was reported in three mice. In the 40 mg/Kg group, 9/10 mice were considered long-term survivors and partial tumor regression was reported in three mice. In the 60 mg/Kg group, 8/10 mice were considered long-term survivors and partial tumor regression was reported in seven mice.

Compound 5 was administered by i.p. injection alone at 15 mg/Kg on a q3dx5 schedule. A T–C value of 21 days was calculated for this group which was found to be statistically significant compared with control (p=0.002). In this group 3/10 mice were considered long-term survivors and partial tumor regression was reported in five mice. The efficacy of this dose level produced half the number of long term survivors as 20 mg/Kg of Compound 15.

Figure 2:
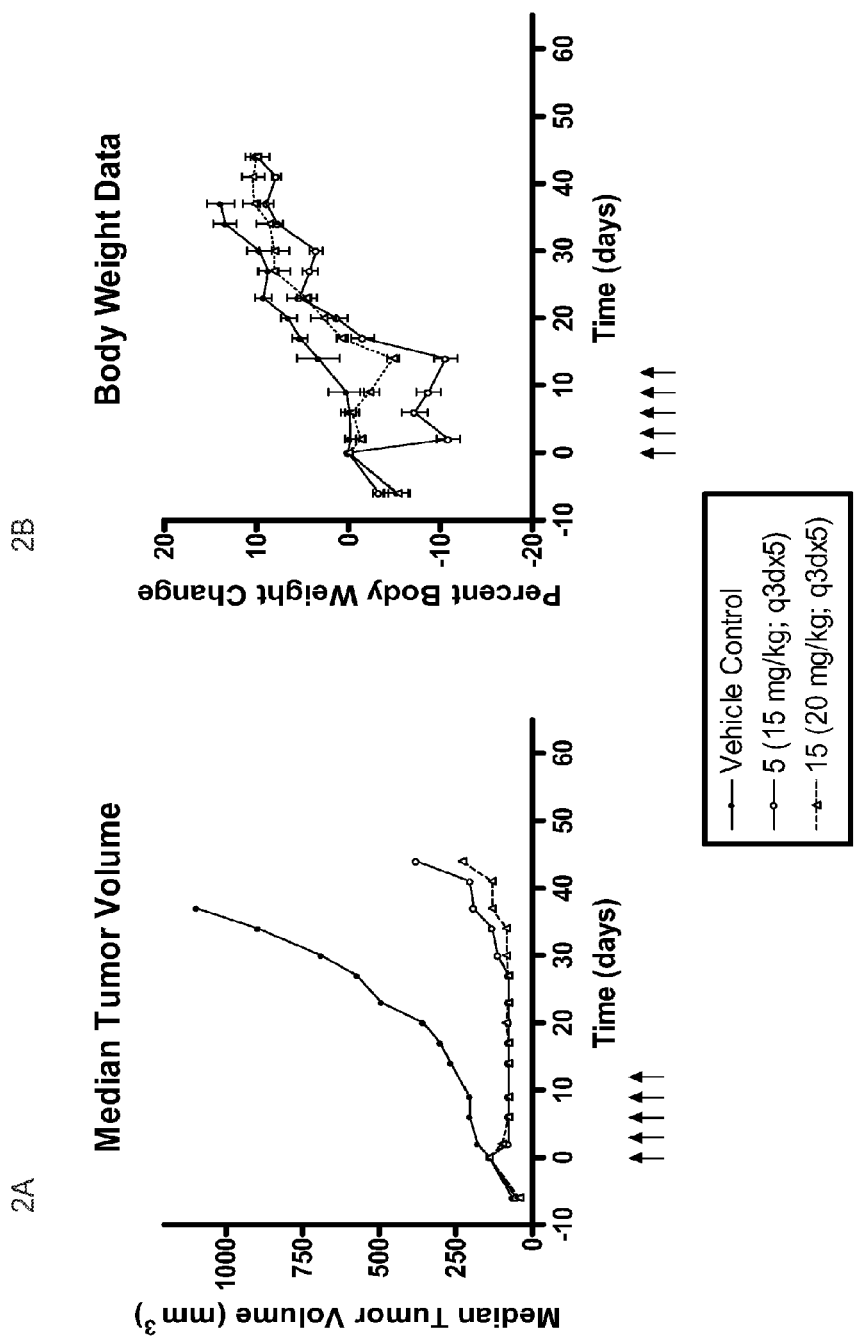
FIG. 2 shows mean tumor volume (2A) and body weight change (2B) resulting from treatment of human xenografts in nude mice with SMAC mimetics substantially as described in Example 5.

The results of the MDA-MB-231 xenograft assay are shown in FIGS. 2A and 2B. Compound 15 at 20 mg/Kg had comparable anti-tumor activity to Compound 5 at 15 mg/Kg. Subsequent studies have shown that the minimal effective dose of Compound 15 in this model is less than 1 mg/Kg. Weight loss was greater in the mice administered Compound 5 at 15 mg/Kg when compared to the mice dosed with Compound 15 at 20 mg/Kg. Thus, Compound 15 has comparable efficacy with less toxicity relative to Compound 5 and therefore has an improved therapeutic index.

The compound of Formula 1 is particularly well tolerated and well suited for use in a pharmaceutical composition, as well as in a method for treating a proliferative disorder or an autoimmune disorder. In particular, the pharmaceutical composition of the invention for the treatment of a proliferative disorder, which comprises an effective amount of Compound 15 in addition to at least one pharmaceutically acceptable excipient, can improve therapeutic index by reducing toxicities. The reduced toxicities include, e.g., one of, or any combination of one or more of:
reduced body weight loss,
decreased incidence of mortality,
reduced bone marrow hypocellularity of the erythroid series,
reduced hypercellularity of the myeloid series,
reduced hypertrophy and hyperplasia of megakaryocytes,
reduced diffuse hypertrophy/hyperplasia of Type 2 pneumocytes
decreased lethargy,
more regular respiration,
lessened increase in heart rate.

The reduced toxicities listed above are those observed in the animals tested. Similar, additional, or different reduced toxicities will be observed in humans. The reductions are relative, e.g., relative to the extent that toxicities would be observed following internal administration of a pharmaceutical composition in which the active pharmaceutical ingredient is an analog of Compound 15, e.g., one or more of the analogs in which R5 is —CH2CH3, —CH(CH3)CH3, —R—CH(OH)CH3, —S—CH(OH)CH3, and —R—CH(OCH3)CH3, e.g., at the same dose or at a dose of comparable potency.

It is understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A method of treating cancer in a mammal in need thereof that comprises administering to the mammal an effective amount of Compound 15 of the following formula:

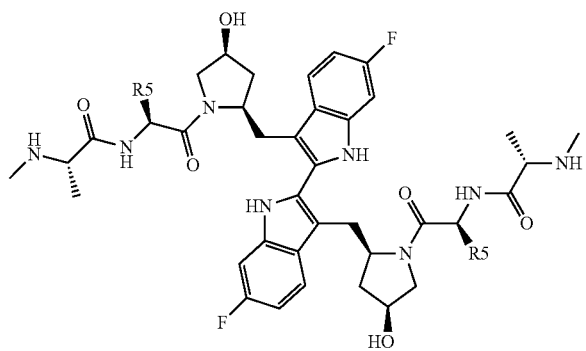

where R5 is —CH$_2$CH$_3$, or a pharmaceutically acceptable salt thereof, in combination with a second cancer therapy that is chemotherapy.

2. The method of claim 1 wherein the cancer is ovarian cancer.

3. The method of claim 1 wherein the chemotherapy comprises administration of a platinum containing DNA modifying agent.

4. The method of claim 2 wherein the chemotherapy comprises administration of a platinum containing DNA modifying agent.

5. The method of claim 3 wherein the chemotherapy comprises administration of carboplatin, cisplatin, or oxaliplatin.

6. The method of claim 4 wherein the chemotherapy comprises administration of carboplatin, cisplatin, or oxaliplatin.

7. The method of claim 1 wherein the chemotherapy comprises administration of carboplatin.

8. The method of claim 2 wherein the chemotherapy comprises administration of carboplatin.

9. A method for inducing apoptosis in a cancer cell comprising contacting the cell with Compound 15 of the following formula:

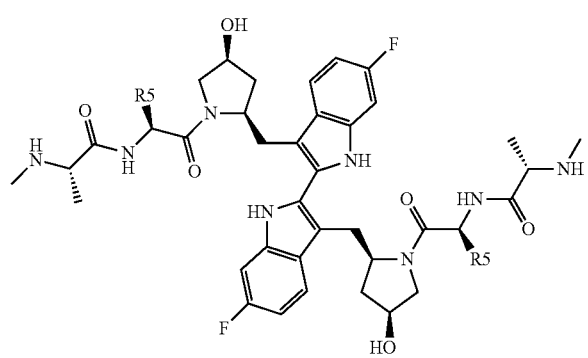

where R5 is —CH₂CH₃, or a pharmaceutically acceptable salt thereof, and also contacting the cell with a second cancer therapy that is chemotherapy.

10. The method of claim 9 wherein the cancer cell is an ovarian cancer cell.

11. The method of claim 9 wherein the chemotherapy comprises administration of a platinum containing DNA modifying agent.

12. The method of claim 10 wherein the chemotherapy comprises administration of a platinum containing DNA modifying agent.

13. The method of claim 9 wherein the chemotherapy comprises administration of carboplatin, cisplatin, or oxaliplatin.

14. The method of claim 9 wherein the chemotherapy comprises administration of carboplatin.

15. The method of claim 10 wherein the chemotherapy comprises administration of carboplatin.

16. The method of claim 1 wherein Compound 15 is administered by intravenous infusion.

17. The method of claim 1 wherein Compound 15 is administered by intravenous bolus.

* * * * *